United States Patent
Butler et al.

(10) Patent No.: US 7,318,825 B2
(45) Date of Patent: Jan. 15, 2008

(54) DYNAMIC CERVICAL PLATES AND CERVICAL PLATE CONSTRUCTS

(75) Inventors: Michael S. Butler, Fishers, IN (US); Michael J. Milella, Jr., Schaumburg, IL (US)

(73) Assignee: Life Spine LLC, Hoffman Estates, IL (US)

( * ) Notice: Subject to any disclaimer, the term of this patent is extended or adjusted under 35 U.S.C. 154(b) by 0 days.

(21) Appl. No.: 11/022,461

(22) Filed: Dec. 22, 2004

(65) Prior Publication Data

US 2005/0137597 A1    Jun. 23, 2005

Related U.S. Application Data

(60) Provisional application No. 60/531,657, filed on Dec. 22, 2003.

(51) Int. Cl.
*A61B 17/58* (2006.01)

(52) U.S. Cl. ................................................. 606/71

(58) Field of Classification Search .................. 606/61, 606/69–71
See application file for complete search history.

(56) References Cited

U.S. PATENT DOCUMENTS

| | | | |
|---|---|---|---|
| 5,616,142 A * | 4/1997 | Yuan et al. ................ 606/61 |
| 5,951,558 A | 9/1999 | Fiz | |
| 6,193,721 B1 * | 2/2001 | Michelson ................ 606/70 |
| 6,224,602 B1 | 5/2001 | Hayes | |
| 6,228,085 B1 | 5/2001 | Theken et al. | |
| 6,258,089 B1 | 7/2001 | Campbell et al. | |
| 6,273,889 B1 | 8/2001 | Richelsoph | |
| 6,306,136 B1 | 10/2001 | Baccelli | |
| 6,364,881 B1 | 4/2002 | Apgar et al. | |
| 6,398,783 B1 | 6/2002 | Michelson | |
| 6,402,756 B1 | 6/2002 | Ralph et al. | |
| 6,413,259 B1 | 7/2002 | Lyons et al. | |
| 6,428,542 B1 | 8/2002 | Michelson | |
| 6,454,769 B2 | 9/2002 | Wagner et al. | |
| 6,503,250 B2 | 1/2003 | Paul | |
| 6,533,786 B1 | 3/2003 | Needham et al. | |
| 6,599,290 B2 | 7/2003 | Bailey et al. | |
| 6,602,257 B1 | 8/2003 | Thramann | |
| 6,620,163 B1 | 9/2003 | Michelson | |
| 6,669,700 B1 | 12/2003 | Farris et al. | |
| 6,695,846 B2 | 2/2004 | Richelsoph et al. | |
| 2001/0041894 A1 | 11/2001 | Campbell et al. | |
| 2002/0045896 A1 | 4/2002 | Michelson | |
| 2002/0045899 A1 | 4/2002 | Errico et al. | |
| 2002/0111630 A1 | 8/2002 | Ralph et al. | |
| 2002/0120273 A1 | 8/2002 | Needham et al. | |
| 2002/0128655 A1 | 9/2002 | Michelson | |
| 2002/0147450 A1 | 10/2002 | LeHuec et al. | |
| 2002/0151899 A1 | 10/2002 | Bailey et al. | |

(Continued)

*Primary Examiner*—Eduardo C. Robert
*Assistant Examiner*—Michael J Araj
(74) *Attorney, Agent, or Firm*—Foley & Lardner LLP

(57) ABSTRACT

N-level internally dynamizing cervical plates and cervical plate constructs in accordance with the present principles, provide unconstrained sliding interconnection between the various plate components after installation on a cervical spine. A tongue-and-groove configuration between the various plate segments provides a constant thickness over the dynamizing portions. Detents provided relative the tongue-and-groove portions allows the various plate components to be permanently joined, but movable relative to one another. Various bone screw anti-backing, anti-rotation or locking devices for cervical bone plates are also provided that allow releasable locking of bone screws relative to the cervical plate.

22 Claims, 25 Drawing Sheets

U.S. PATENT DOCUMENTS

| | | |
|---|---|---|
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0023242 A1 | 1/2003 | Harrington, Jr. |
| 2003/0040749 A1 | 2/2003 | Grabowski et al. |
| 2003/0060828 A1 | 3/2003 | Michelson |
| 2003/0083658 A1 | 5/2003 | Hawkes et al. |
| 2003/0105462 A1 | 6/2003 | Haider |
| 2004/0034356 A1 | 2/2004 | LeHuec et al. |
| 2004/0068319 A1 | 4/2004 | Cordaro |
| 2004/0087951 A1 | 5/2004 | Khalili |
| 2004/0102773 A1 | 5/2004 | Morrison et al. |
| 2004/0106924 A1* | 6/2004 | Ralph et al. .................. 606/71 |
| 2004/0122426 A1 | 6/2004 | Michelson |
| 2004/0127896 A1 | 7/2004 | Lombardo et al. |
| 2004/0127897 A1 | 7/2004 | Freid et al. |
| 2004/0127899 A1 | 7/2004 | Konieczynski et al. |
| 2004/0181226 A1 | 9/2004 | Michelson |
| 2004/0181229 A1 | 9/2004 | Michelson |
| 2004/0186476 A1 | 9/2004 | Michelson |
| 2004/0204712 A1 | 10/2004 | Kolb et al. |
| 2004/0220571 A1 | 11/2004 | Assaker et al. |
| 2004/0220572 A1 | 11/2004 | Michelson |
| 2004/0236335 A1 | 11/2004 | Michelson |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0043732 A1 | 2/2005 | Dalton |
| 2005/0059971 A1 | 3/2005 | Michelson |
| 2005/0075699 A1 | 4/2005 | Ross |
| 2005/0149026 A1 | 7/2005 | Butler et al. |
| 2006/0224241 A1 | 10/2006 | Butler et al. |
| 2007/0118122 A1 | 5/2007 | Butler et al. |

* cited by examiner

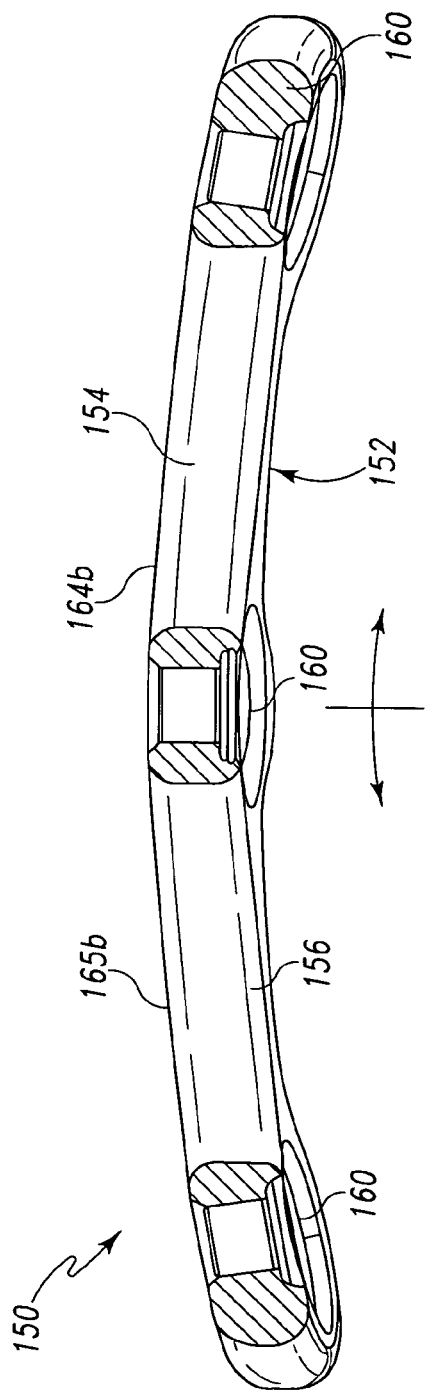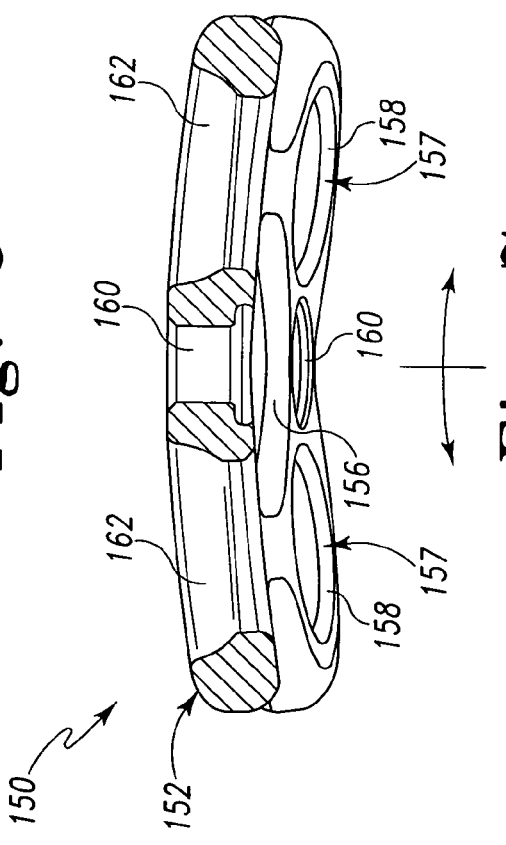
Fig. 6
Fig. 7

DYNAMIC CERVICAL PLATES AND CERVICAL PLATE CONSTRUCTS

This U.S. non-provisional patent application claims the benefit of and/or priority to U.S. provisional patent application Ser. No. 60/531,657 filed Dec. 22, 2003 entitled "Static and Dynamic Cervical Plate Construct", the entire contents of which is specifically incorporated herein by reference.

BACKGROUND OF THE INVENTION

1. Field of the Invention

The present invention relates generally to devices for the internal fixation of the spine particularly within the fields of orthopedics and/or neurosurgery such as spinal implants for holding vertebral bones fixed relative to one another and, more particularly, to static and/or a dynamic bone fixation implants for use in spinal surgical procedures for stabilizing the relative motion of, temporarily or permanently immobilizing, bones of the spine.

2. Background Information

Cervical plates have been used for more than 20 years to increase neck stability following single and multi-level cervical surgery. Cervical plates, implanted during surgery for reasons such as disease, trauma, defect, accident or the like, are used to stabilize one or more cervical vertebrae. Stabilization leads to a proper healing or a desired outcome. The cervical plate is mounted to one or more vertebrae during the surgery. Typically, screws are used to mount the cervical plate to the one or more vertebrae. It is important during the mounting process that the plate be properly aligned on the vertebrae for receipt of the mounting screws.

In some instances, it is desirous to cause the fusion of two adjacent vertebrae. If this is the case, the surgeon makes a small incision in the front of the neck to reach the cervical spine. Tissues and muscles are retracted (spread apart) to reveal the proper level in the cervical spine. The cartilaginous material or disc between the two vertebrae is removed and the bone surface abraded to encourage a bleeding surface. Blood from the bleeding surfaces is desired in order for the bones to fuse. The space between the adjacent vertebrae is filled with bone graft. A cervical plate is then screwed into the superior (top) and inferior (bottom) vertebrae. This stabilizes the cervical spine to facilitate fusion and healing. With current cervical plates however, once the plate is secured over the graft area, the only manner of accessing the graft area is to remove the plate. Moreover, with current cervical plates, it is necessary to provide the bone graft material before mounting the plate.

Heretofore, cervical plates were almost exclusively static, in that they have fixed dimensions. It has been realized that it is desirable in certain situations to allow shifting or slight movement between the plate-mounted vertebrae. The prior art is relatively devoid of dynamic cervical plates.

It is thus evident from the above that what is needed is a cervical plate that allows access to a bone graft area of a cervical surgical site.

It is thus further evident from the above that what is needed are various dynamic cervical plates and dynamic cervical plate constructs.

This need and others are accomplished through application of the principles of the subject invention and/or as embodied in one or more various forms and/or structures such as are shown and/or described herein.

SUMMARY OF THE INVENTION

N-level internally dynamizing cervical plates and cervical plate constructs in accordance with the present principles, provide unconstrained sliding interconnection between the various plate components after installation on a cervical spine. The N-level dynamic cervical plate has a tongue-and-groove configuration between the various plate component or segments thereof that provides a constant thickness over the dynamizing portions. A graft window is defined extending between each pair of bone screw bores, with a pair of bone screw bores disposed on each plate component. Detents provided relative the tongue-and-groove portions allows the various plate components to be permanently joined, but movable relative to one another. Various bone screw anti-backing, anti-rotation or locking devices for cervical bone plates are also provided that allow releasable locking of bone screws relative to the cervical plate.

In one form of the invention, a three-component, two level dynamic cervical bone plate is configured such that a middle component accepts an identical end component at both ends of the middle component via a mutual tongue and groove configuration. The end component may be a 180° interchangeable part. The middle component may be a 180° interchangeable part. The middle component and the end component have cooperating configurations and complimentarily configured tongue and groove structures that allow sliding movement between the middle component and the end components. The 2-L dynamic plate in accordance with the principles of the subject invention provides for pure vertebral body translation without creating guesswork with respect to screw positioning.

As well, in another form of the invention, there is provided a kit for assembling an N-level dynamic cervical plate. The kit includes a middle component and two, identical end components. The end components is slidingly assembled to each longitudinal end of N number of extension components to provide a dynamic N level (N-L) cervical plate that includes a graft window between each level, pair of bone screws on each component, or as formed between the components as graft window portions or segments thereof. Moreover, the end components are configured such that they present the same interconnectivity to the middle component when rotated 180° relative to a plane defined by the body thereof.

The present invention provides advantages over the teachings of the prior art with respect to cervical plating technology. The principles accompanying the present invention allows the fixation plate to be used with greater accuracy. This may ultimately increase the efficacy of an established procedure. For instance the present invention provides a window within the center area of the plate. This allows viewing of graft material during and after placement. Such is accomplished by utilizing a constant plate surface area thickness tongue and groove interface that is angled in one plane and curved in a perpendicular plane for both the static and dynamic plates, and for all levels (1-L, 2-1, N-L) of fixation plates.

BRIEF DESCRIPTION OF THE DRAWINGS

The above mentioned and other features and objects of this invention, and the manner of attaining them, will become more apparent and the inventions will be better understood by reference to the following description of embodiments of the inventions taken in conjunction with the accompanying drawings, wherein:

FIG. 6 is a sectional view of the 2-L static bone fixation plate of FIG. 5 taken along line 6-6 thereof;

FIG. 7 is a sectional view of the 2-L static bone fixation plate of FIG. 5 taken along line 7-7 thereof;

Figure 1:
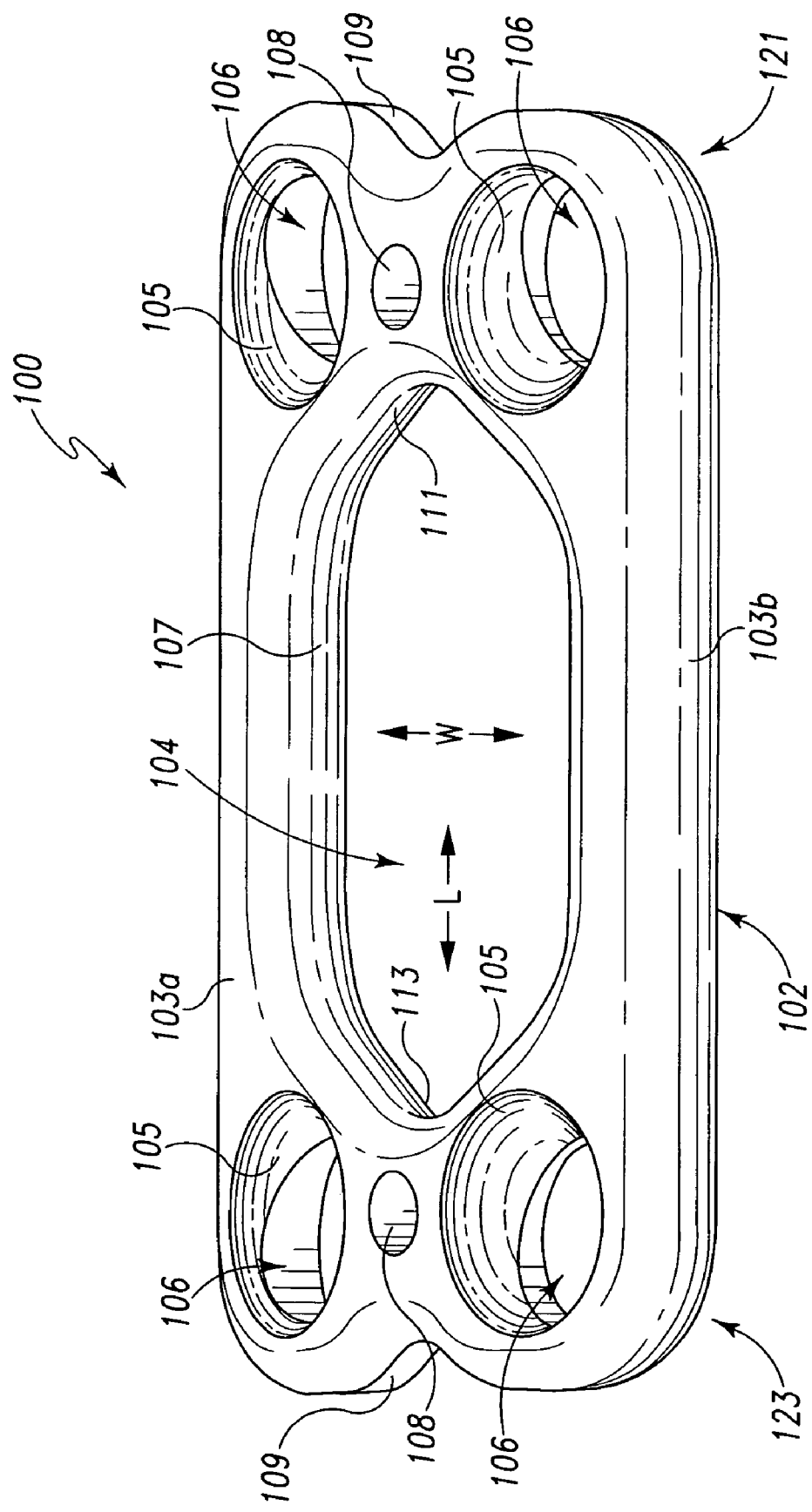
FIG. 1 is a perspective view of an exemplary embodiment of a one-level (1-L) static bone fixation plate fashioned in accordance with the principles of the present invention.

Corresponding reference characters indicate corresponding parts throughout the several views. Although the drawings represent various embodiments of the invention, the drawings are not necessarily to scale and certain features may be exaggerated in order to better illustrate and explain the invention. Also, the exemplifications set out herein illustrate various embodiments of the invention, but such exemplifications are not to be construed as limiting the scope of the invention in any manner.

DETAILED DESCRIPTION OF THE INVENTION

Figure 2:
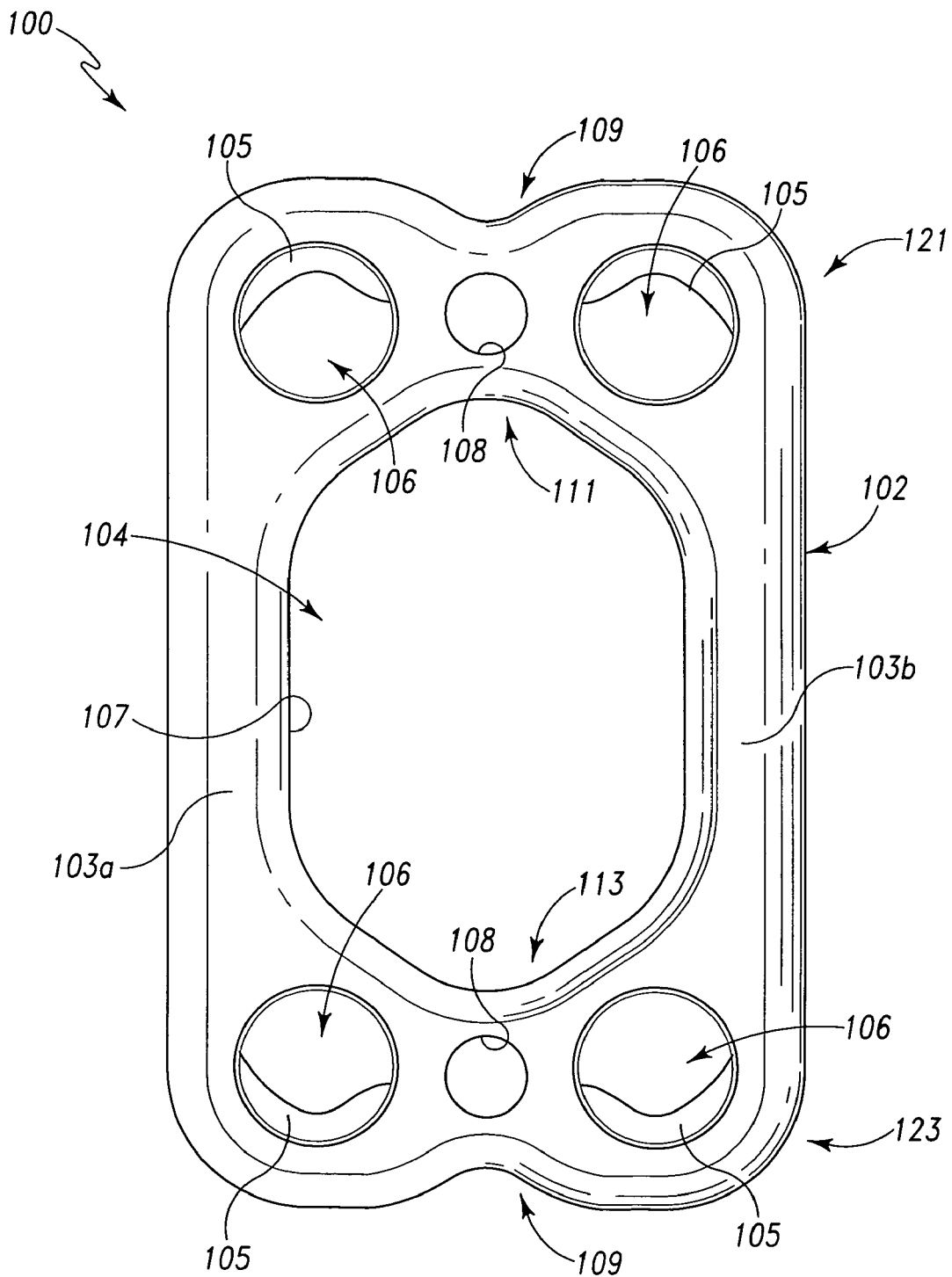
FIG. 2 is a bottom view of the one-level (1-L) static bone fixation plate of FIG. 1.

Referring to FIGS. 1 and 2, there is depicted an exemplary one level (1-L), static cervical plate generally designated 100, of which FIG. 1 is lateral perspective view of the plate 100 and FIG. 2 is a bottom plan view of the plate 100. The plate 100 is characterized by a body 102 formed of a suitable material such as is known for the manufacture of cervical plates, for example titanium, a titanium alloy or the like. The body 102 is generally rectangular in shape and slightly curved on the underside thereof in order to mimic the natural curvature of a vertebra. Such curvature may be in one or two planes. The body 102 may be manufactured in various sizes to accommodate vertebra of different sizes.

The body 102 has an opening, window, void or the like 104 (collectively hereinafter, window) in a middle, center or central portion of the body 102 bounded by surface 107. While the window 104 may be formed in various configurations, it is preferable that the window extend essentially from proximate to adjacent bone screw bores 106 that are situated on ends 121, 123 of the 1-L plate 100. In the exemplary plate 100, the window 104 is configured in a somewhat oblong shape defining a first peak 111 and a second peak 113. As developed more fully below, the elongation of the window allows for better alignment of the plate 100 on the vertebra by the surgeon. The window 104 itself provides visualization of the bone graft abutment to the posterior section of the plate while in situ. The opening 104 defines a first leg 103a and a second leg 103b to the body 102 that extend between ends 121 and 123 of the body 102. The length (l) is longer then the width (w) of the opening 104. The length (l) is elongated or extended to span essentially between the edges of each screw bore 106.

The window/leg configuration creates a "dual pillar" like support foundation for plate strength as between the first and second ends 121, 123, such as against twisting or flexing. The size and configuration of the window 104 (forming two legs or a dual pillar configuration) provides an easy bone screw placement and/or allows for bone graft viewing. Each leg 103a/103b preferably, but not necessarily, has the same cross-sectional profile. Moreover, the cross-sectional profile of each leg is preferably, but not necessarily, consistent throughout its length between ends 121, 123. Furthermore, the legs 103a/103b have the same height profile as the overall plate body 102.

The ends 121 and 123 each have two bone screw bores 106 each one of which is disposed on corners of the respective ends. The four bone screw bores 106 are preferably, but not necessarily, aligned to correspond to vertices of a rectangle, the rectangle preferably, but not necessarily, being a scaled version of the rectangular body 102. The scaled rectangle forming a pattern for placement of screw bores on a patient's vertebra. The ends 121 and 123 each have an outer contour that defines a notch 109. Each bone screw bore 106 is sized, configured and/or situated such that a portion thereof is adjacent a proximate portion of the opening 104.

Each bone screw bore 106 has a ledge 105 formed in the interior thereof. The ledge 105 is configured to capture an undersurface of a head of a bone screw. As such, each ledge 105 is somewhat dish-shaped to accommodate the complementary shape of the undersurface of the bone screw head. Each ledge 105 is also angled to allow the inserted bone screw to achieve a proper orientation during implantation. The bone screw bores 106 are configured to utilize various types of bone screws such as fixed angle screws, emergency screws, and variable angle screws, examples of which are incorporated herewith through the parent provisional application. Moreover, the bore/ledge allows variable bone screw angulation while fixing or mounting the plate to the vertebrae. Such angulation is up to 30° cephalad—caudal, and 20° lateral—medial.

The body 102 further includes two bores 108 each one of which is situated proximate (here shown as between) bone screw bore pairs 106 of each end 121 and 123. Each bore 108 is configured to receive a boss or fastening device/portion of a bone screw retainer device, cover plate, retention clip, or the like such as described herein for preventing rotation and/or backout of a bone screw that has been implanted.

Figure 3:
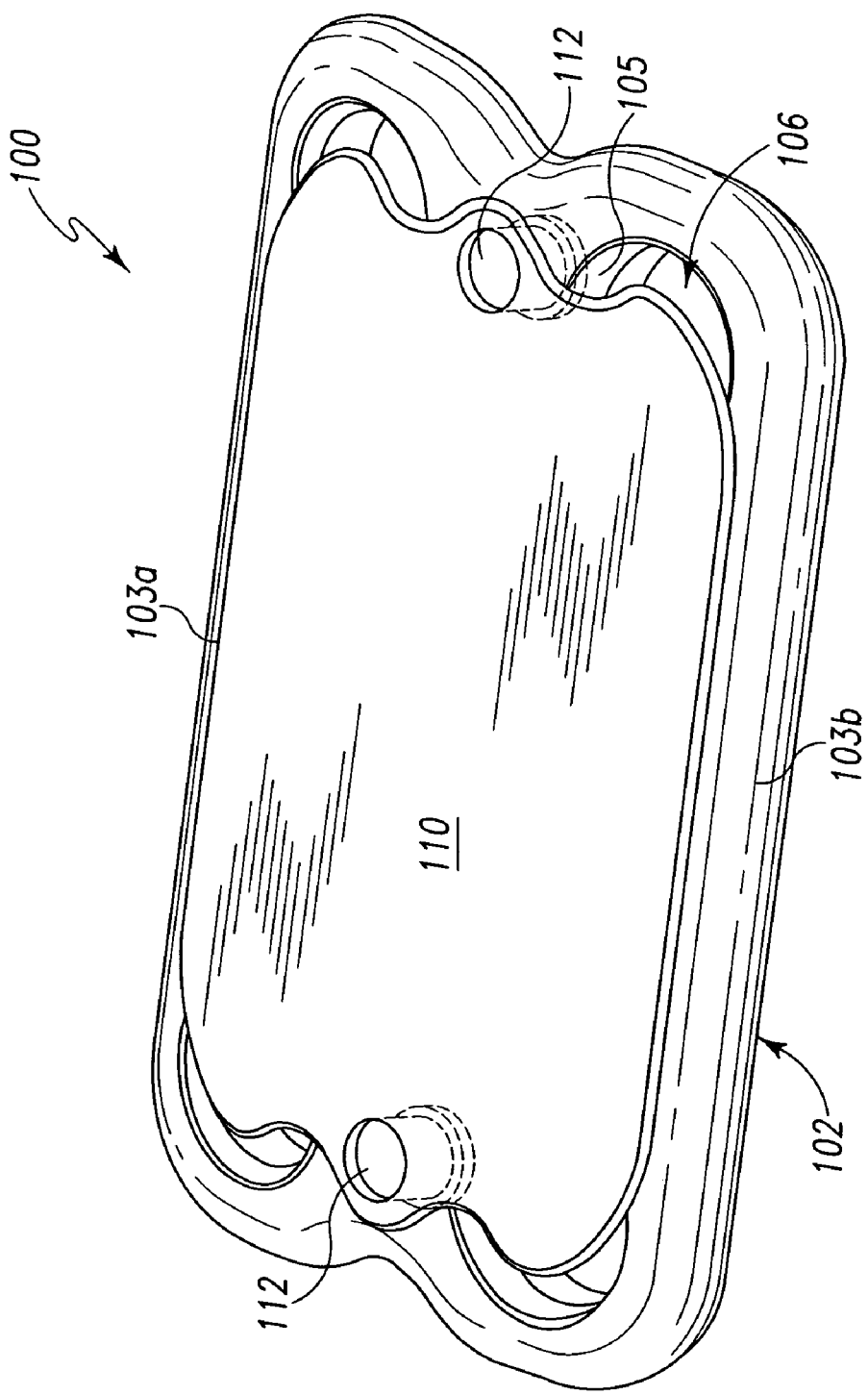
FIG. 3 is a perspective view of the one-level (1-L) static bone fixation plate of FIG. 1 but having a cover thereon fashioned in accordance with an aspect of the present invention.

Referring to FIG. 3, there is depicted the 1-L static cervical plate 100 of FIGS. 1 and 2, but shown with one embodiment of a bone screw anti-backout, rotation inhibitor and/or releasable locking mechanism, embodied as a cover, plate or the like 110. The cover 110 is situated on the plate 100 so as to cover the graft window 104 and at least partially the heads of the implanted bone screws. The cover 110 is used with the plate 100 to provide an embodiment of a 1-L static cervical plate construct. After the plate 100 has been implanted through use of bone screws, such as via the procedure described herein, the cover 110 may be placed onto the body 102. This covers the opening 104, and most of the screw bores 106. The cover 110 is essentially flat, thus having a low profile.

The cover 110 moreover surrounds the window 104 and most of each bone screw bore 106 (which would be most of a bone screw head when so installed). This helps to keep, retain or releasably lock the bone screws from backing out and/or turning. The cover also will provide protection against potential graft migrating out of the inter-vertebral space post operatively. The cover further will allow for post-operative visualization via radiograph. The cover 110 includes two cover bosses 112 that are configured to provide a snap fit into plate bores 108 when installed, such that the cover 110 is retained on the plate 100. While normal use will not cause the cover 110 to separate from body 102, a simple tool may allow removal of the cover 110.

The cover 110 is exemplary of the type of covers that may be used as bone screw locking mechanisms with the 1-L static cervical plate 100. As such, covers 110 may be manufactured in various sizes to accommodate various sizes of cervical plates 110. The cover 110 is also fabricated from a biocompatible material like the material for the plate 100. The plate 100 may also accommodate other styles of covers.

Figure 4:
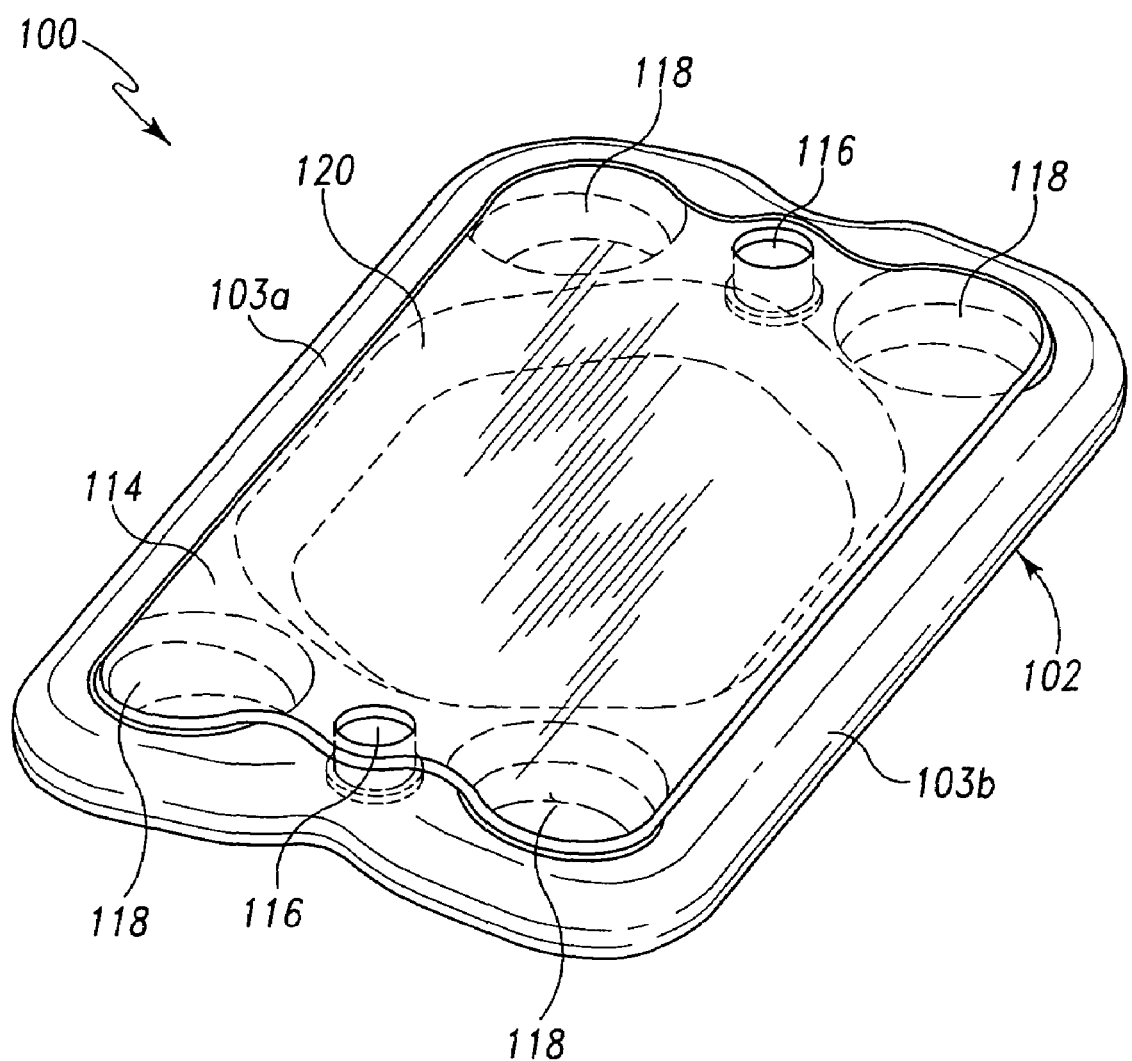
FIG. 4 is a perspective view of the one-level (1-L) static bone fixation plate of FIG. 1 having a contoured cover thereon fashioned in accordance with an aspect of the present invention.

FIG. 4 depicts an alternative cover 114 (bone screw locking mechanism and/or graft window/area cover) for the 1-L static cervical plate 100 of FIG. 1. The cover 114 includes two bosses 116 that are configured to be snap fit received in the plate bores 108 thus retaining the cover 114 onto the plate 100. The cover 114 extends over the opening 104 of the plate from over the leg 103a to over the leg 103b, and over each screw bore 106 of the body 102.

In this embodiment, the cover 114 includes a depression or concavity 120 that is configured like the opening 104 in order to extend into the opening 104 when the cover 114 is installed. Moreover, the cover 114 includes four screw bore depressions or concavities 118 each of which is configured to extend into one of the bone screw bores 106 of the body 102 of the plate 100. The covers or cover plates may be fashioned from an alloy of metals, titanium, a titanium alloy, PEEK, or suitable biocompatible material.

While none of FIGS. 1-4 show a bone screw in use with the plate 100, it should be appreciated that the plate 100 is able to utilize various types of bone screws such as were set forth in the corresponding provisional application, incorporated above. Briefly, the plate 100 may utilize a polyaxial bone screw, a fixed bone screw, and an emergency bone screw.

Figure 5:
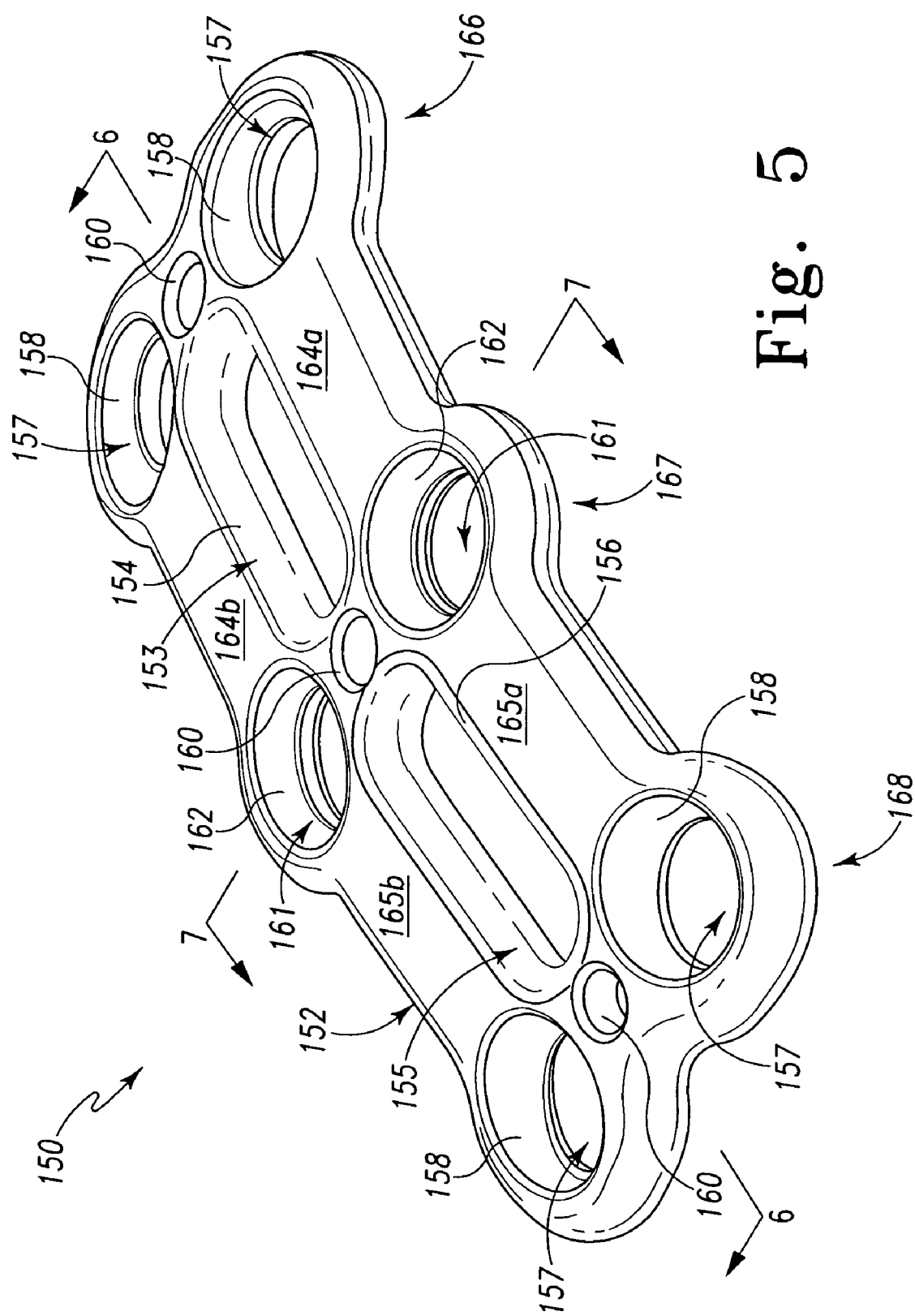
FIG. 5 is a perspective view of an exemplary embodiment of a two-level (2-L) static bone fixation plate fashioned in accordance with the principles of the present invention.

Referring now to FIGS. 5-7, there is depicted an exemplary embodiment of a two level (2-L) static cervical plate, generally designated 150, incorporating the dual or twin pillar configuration for each level thereof such as described with reference to the 1-L plate 100. The 2-L plate is designed to span between and be anchored to three vertebrae with a central window in accordance with the present principles between each fastening juncture thereof. The windows formed by the dual pillar configuration. As indicated in FIGS. 6 and 7 by the curved arrow relative to a horizontal line (representing a centerline of the plate 100) illustrates two planes of curvature that the plate 100 may have mimicking the curvatures of vertebrae. As such, a particular length and/or thickness cervical plate may also be manufactured with varying curvatures.

The plate 150 is defined by a body 152 that may be considered as having a middle portion or section 167, a first end portion or section 166 on one side of the middle portion 167, and a second end portion or section 168 on another side of the middle portion 167. The middle portion 167 defines a fastening, mounting or attachment portion that is adapted to be attached to a central vertebra of a three vertebrae fusion. The end portions 166 and 168 also define a fastening, mounting or attachment portion that is adapted to be attached to separate outer vertebra of the three vertebrae fusion. As such, and keeping with the principles set forth herein with respect to the 1-L static plate 100, the static 2-L plate 150 includes dual (two) openings, windows, voids or the like 153 and 155, one opening for each level or between each end portion 166, 168 and the middle portion 167. Each window 153 and 155 is centrally, located defines leg pairs (pillars) 164a/164b and 165a/165b.

The opening 153 is disposed in the middle, center or central portion of the area between the end portion 166 and the middle portion 167, being bounded by surface 154. The window 153 is configured in an exemplary fashion as an elongated oval that extends from just adjacent to a portion of each screw bore 157 of the end portion 166 (proximate the reception bore 160 of the end portion 166) to just adjacent to a portion of each screw bore 161 of the middle portion 167 (proximate the reception bore 160 of the middle portion 167).

The opening 155 is disposed in the middle, center or central portion of the area between the end portion 168 and the middle portion 167, being bounded by surface 156. The opening 155 is configured as an elongated oval that extends from just adjacent to a portion of each screw bore 157 of the end portion 168 (proximate the reception bore 160 of the end portion 168) to just adjacent to a portion of each screw bore 161 of the middle portion 167 (proximate the reception bore 160 of the middle portion 167).

The elongation of the openings 153, 155 allow for alignment of the plate 150 during surgery and mounting thereof by the surgeon. The size and configuration of the openings 153, 155 (forming two legs or a dual pillar configuration) provides easy bone screw placement and/or allows for bone graft viewing.

Each leg pair 164a/164b and 165a/165b preferably, but not necessarily, has the same cross-sectional profile. As well, each leg 164a/b and 165 a/b preferably, but not necessarily has the same cross-sectional profile. Moreover, the cross-sectional profile of each leg is preferably, but not necessarily, consistent throughout its length between the middle portion 167 and end portions 166 and 168. Furthermore, the legs 164a/b and 165a/b have the same height profile as the overall plate body 152.

The ends 166 and 168 each have two bone screw bores 157 each one of which is disposed on corners of the respective ends and at least partially defining the fastening portions. The ends 166 and 168 each have an outer contour that defines a notch. Each bone screw bore 106 is sized, configured and/or situated such that a portion thereof is adjacent a proximate portion of its respective opening 153, 155. Each bone screw bore 157 has a ledge 158 formed in the interior thereof. Each ledge 158 is configured to capture an undersurface of a head of a bone screw. As such, each ledge 158 is somewhat dish-shaped to accommodate the complementary shape of the undersurface of the bone screw head. Each ledge 158 is also angled to allow the inserted bone screw to achieve a proper orientation during implantation. The bone screw bores 157 are configured to utilize various types of bone screws as described above. Additionally, the bone screw bores 157 are configured to utilize various types of bone screws such as fixed angle screws, emergency screws, and variable angle screws, examples of which are incorporated herewith through the parent provisional application. Moreover, the bore/ledge allows variable bone screw angulation while fixing or mounting the plate to the vertebrae. Again, such angulation may be up to 30° cephalad—caudal, and 20° lateral—medial.

The middle portion 167 also has two bone screw bores 161 disposed as pairs of screw bores in like manner to the other screw bores at least partially defining the fastening portion. Each bone screw bore 161 is sized, configured and/or situated such that a portion thereof is adjacent a proximate portion of an opening 153, 155. Each bone screw bore 161 has a ledge 162 formed around the interior thereof. Each ledge 162 is configured to capture an undersurface of a head of a bone screw. As such, each ledge 158 is somewhat dish-shaped to accommodate the complementary shape of the undersurface of the bone screw head. Each ledge 158 is also designed to receive the inserted bone screw in a fairly straight manner to achieve a proper orientation during implantation. The bone screw bores 161 are configured to utilize various types of bone screws like those above.

The body 152 further includes two bores 160 each one of which is situated between bone screw bore pairs 157 of each end portion 166 and 168. An additional like bore 160 is positioned in the middle portion 167. Each bore 160 is configured to receive a boss or fastener of a bone screw retainer device, cover plate, retention clip, or the like.

Figure 8:
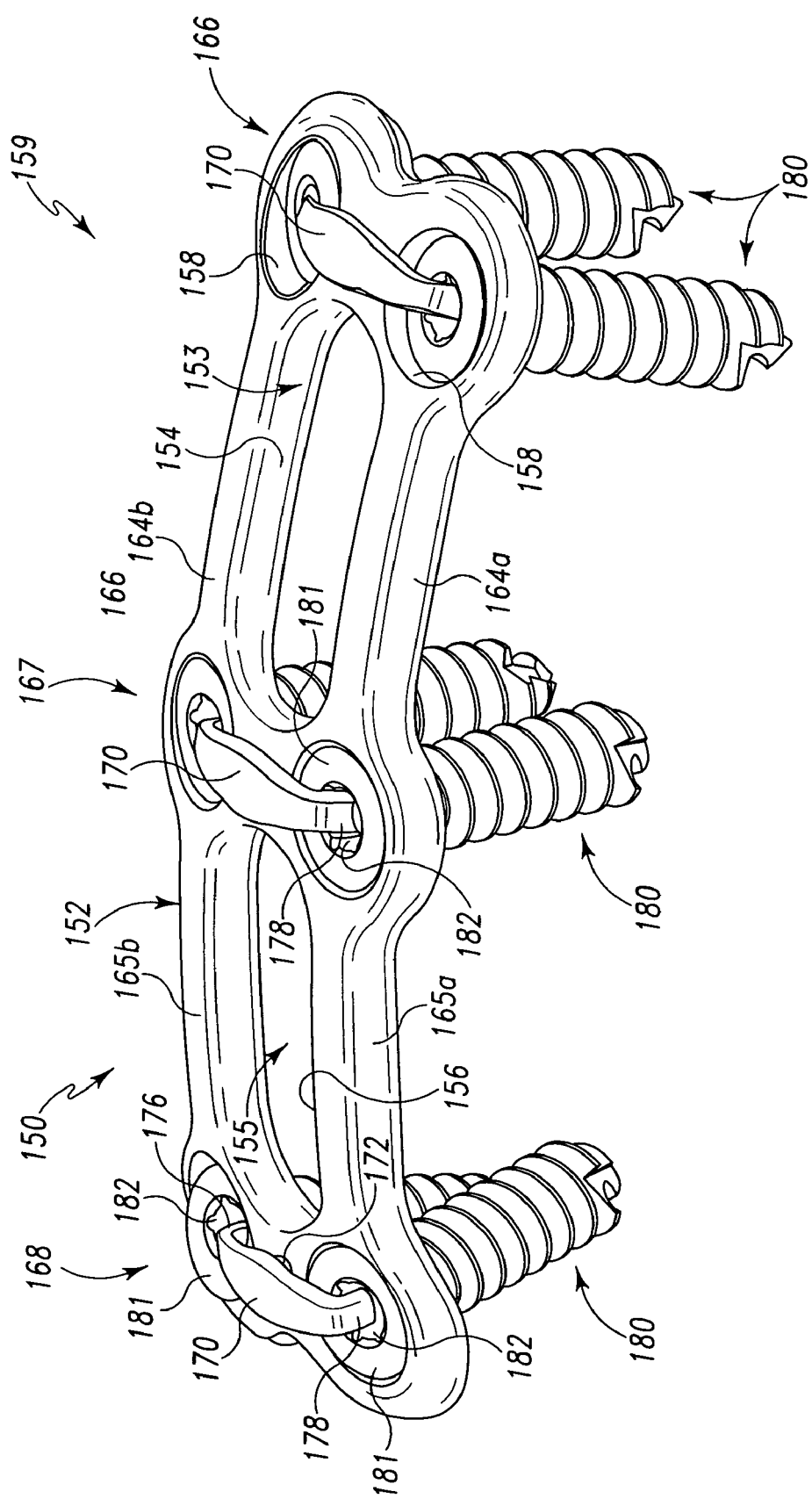
FIG. 8 is a perspective view of a 2-L construct including the 2-L static bone fixation plate of FIG. 5 with bone plate screws and bone screw retention clips.

Referring to FIG. 8, there is depicted an exemplary 2-L static cervical plate construct 159. The 2-L static cervical plate construct 159 includes the 2-L static cervical plate 150, bone screws 180, and bone screw locking, retainer or retention clips, tabs or the like 170 (clips). Some of the bone screws 180 are depicted in various orientations relative to the plate 150 to illustrate the ability of the plate 150 to allow such variable orientations. The construct 159 utilizes releasable bone screw locking means, anti-backing, retainer, retention or retaining clips or tabs 170 that attach onto and between pairs of screws 180, particularly the pairs of screws for each body section 166, 167, 168. The clips 170 also attach to the plate body 152. The clips 170 aid in preventing the backing out or rotation of the bone screws thus providing locking of the bone screws and to the cervical plate.

Figure 9:
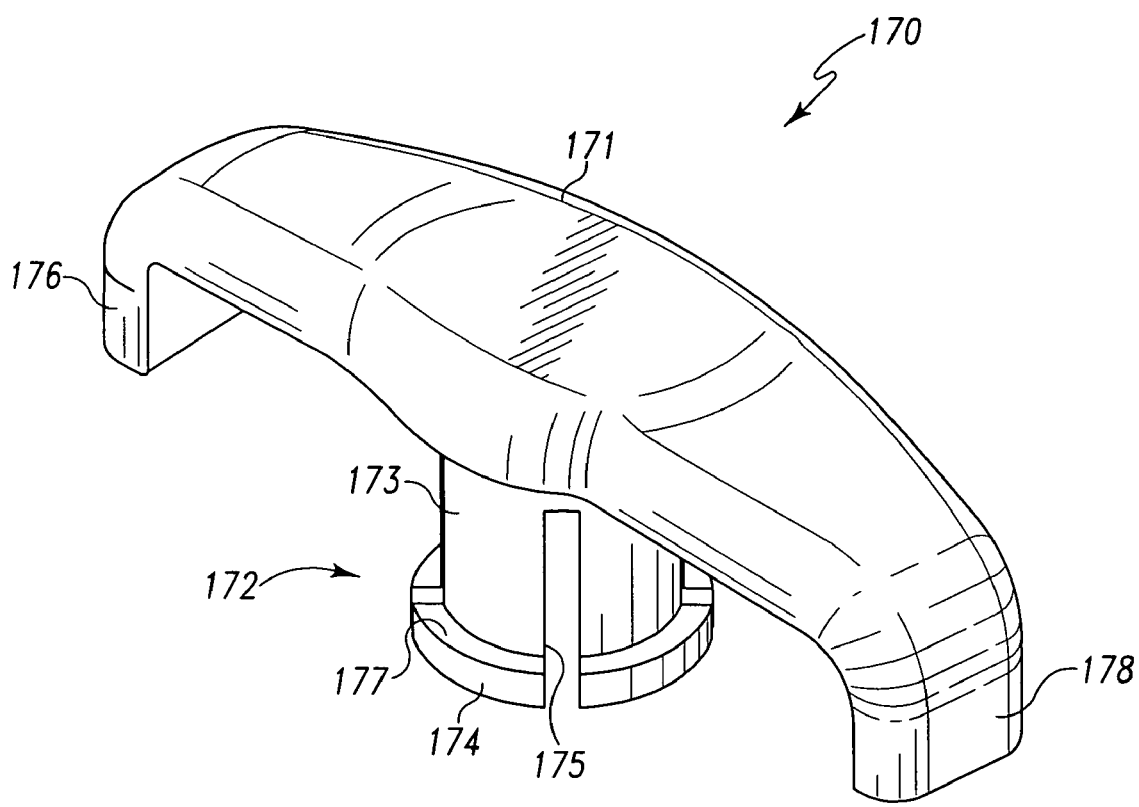
FIG. 9 is an enlarged perspective view of the bone screw retention clip depicted in FIG. 8.

Additionally referring to FIG. 9, a clip 170 is depicted. The clip 170 has been enlarged for clarity. The clip 170 is formed of a biocompatible material preferably, but not necessarily, the same material as the cervical plates and/or cover plates. The clip 170 is defined by a body 171 having a first prong 176 on one end thereof, a second prong 178 on a second end thereof, and a boss structure 172. The body 171 is sized such that the prongs 176 and 178 span the distance between bone screw heads. The boss structure 172 is defined by a post 173 that extends from the underside of the body 171. The post terminates in a rim 174 and includes one or more slots 175. The post 173 is configured to be received in the clip post (boss) bore 160 of the body 152 of the plate 150 (and other such situated bores in the other plates described herein) thus releasably retaining or locking the clip 170 to the plate 150.

Each prong 176, 178 is adapted to be received in a bone screw head socket. It should be appreciated, that the use of clips 170 is not limited to static 2-L plates as shown, but may be used with static 1-L plates, static multi-level plates, and dynamic plates of all levels. The clip 170 is provided in various sizes in order to be used with plates of various sizes, since the span between bone screw heads may be different for different size plates. The clip 170 also has a low profile (thickness) so as to remain relatively flat against the plate 150.

The diameter of the post 173 is slightly less than the diameter of the receiving bore in the plate (e.g. bore 160 of plate 150) so that the receiving bore may receive the post. The rim 174, however, defines a diameter that is oversized for the receiving bore in the plate. The notches or slots 175 allow the ends of the post 173 to slightly compress, reducing the effective diameter of the rim 174, causing the rim 174 to pass through the receiving bore. Once the rim 174 is through the receiving bore, the post 173 returns to its uncompressed state such that the end 177 of the rim 174 contacts the underside of the plate, preventing the clip 170 from pulling out of the receiving bore without a special tool or the like. The resilient boss 174 is thus configured to be releasably, but snugly snap or press fit received into an appropriate plate bore.

The interaction of the clip 170 with the plate 150 and the bone screw pairs is best seen in FIG. 8, and particular attention is drawn to the end portion 168 of the plate 150 of FIG. 8. Each bone screw 180 has a head or head portion 181. Each head 181 includes a socket 182 formed therein. The socket 182 is preferably, but not necessarily, configured in a polygonal pattern. Other configurations may be used. Each corner 182 of the polygon pattern (socket configuration) is rounded such that the span of the ends of the prongs 176, 178 fits into two rounded corners 182. In this manner the prongs 176 and 178 lock the bone screws from rotation. Moreover, rotation of either bone screw of the bone screw pair fitted with a clip 170 will slightly rotate the clip in the plane of the plate 150 thus binding the clip against each other. The clip 170 is also releasably locked to the plate 150.

The boss 172 of the clip 170 is situated in the bore 157 (snap-fit received). One prong 176 extends into the socket 182 of the head 181 of the upper bone screw 180 while the other prong 178 extends into the socket 182 of the head 181 of the lower bone screw 180. The prongs interact with the polygon socket of the head to limit rotation of a screw. The first and second configured flanges 176, 178 are configured to be press or snap fit received in the bone screw head socket.

Figure 10:
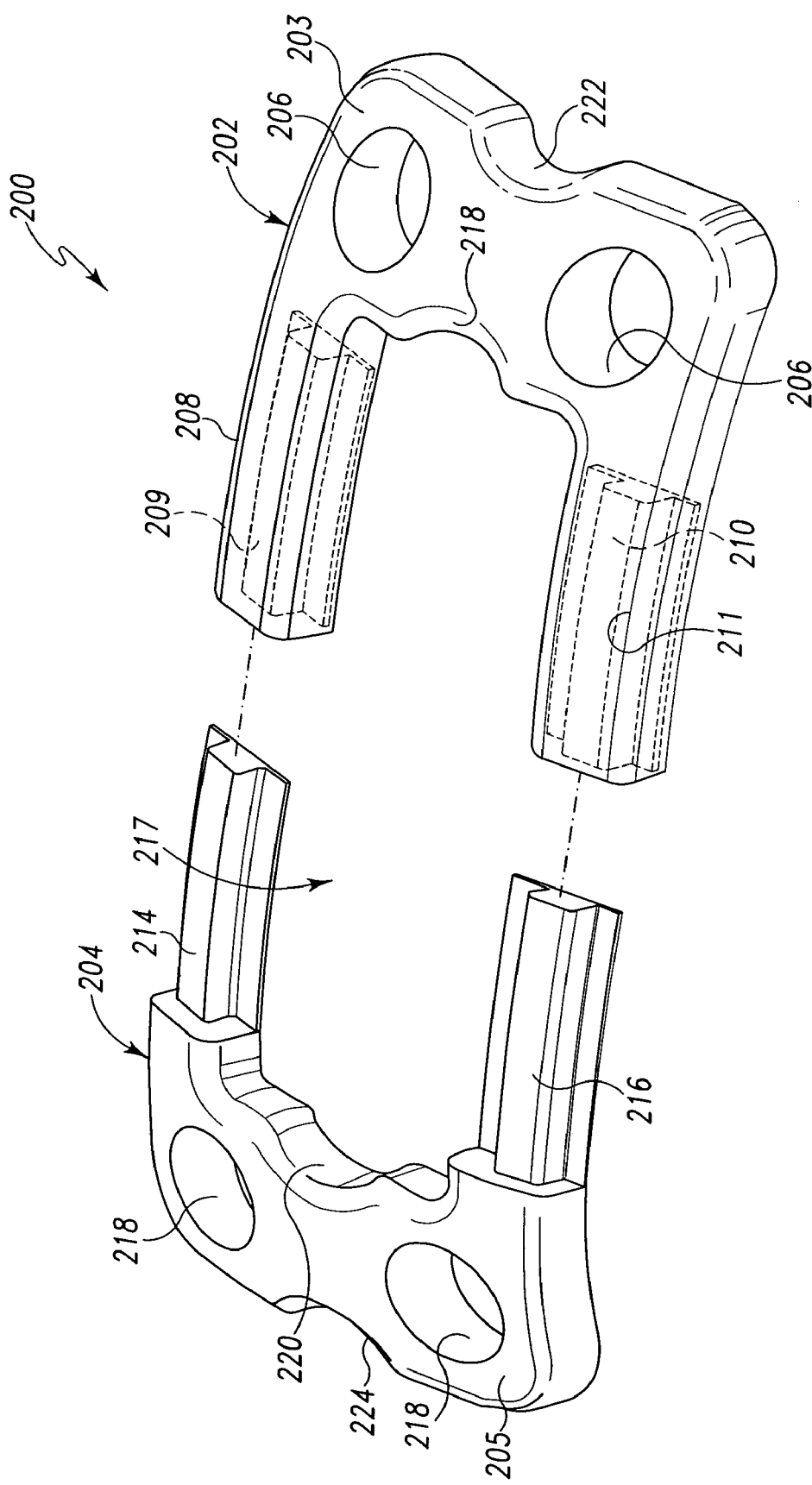
FIG. 10 is a perspective view of an exemplary embodiment of a one-level (1-L) dynamic bone fixation plate fashioned in accordance with the principles of the present invention, the 1-L dynamic plate shown in an almost fully open or fully dynamic state.

FIG. 10 depicts an exemplary embodiment of a dynamic 1-L cervical plate generally designated 200, in accordance with the present principles. The dynamic 1-L plate 200 is shown in exploded form to better illustrate the manner in which the dynamic plate is assembled, joined and/or is dynamic or dynamizes. The dynamic 1-L plate 200 is characterized by a first section 202 and a second section 204 that when assembled or together provides an opening, void or window 117. The size of the opening 117 is variable depending on the position of the two sections 202, 204 relative to one another. Each section 202, 204 defines a U-shape or portion that slidingly mates with one another to provide dynamization when attached. This sliding motion is unconstrained such that it smoothly transitions between various positions without ratchets or the like. The sections 202, 204 each provide a fastening portion, one for each vertebra. The window 217 exposes an area between the vertebrae. It should be appreciated that the configuration of such mating may be modified and/or deviate from that shown.

The first section 202 has a body 203 supporting two bone screw bores 206 which, while not shown, may include configured ledges such as the configured ledges 158 of bone screw bores 157 of plate 150 (see, e.g. FIG. 5) for variable bone screw angulation as described above. The first section 202 also includes first and second legs 208 and 211. The first leg 208 has a configured channel 209 extending therein. The second leg 211 also has a configured channel 210 extending therein. While not necessary, the first and second channels 209, 210 are preferably the same configuration, but may be of one each such that the device is 180° rotatable and be the same.

The second section 204 has a body 205 supporting two bone screw bores 218, which, while not shown, may include configured ledges such as the configured ledges 158 of bone screw bores 157 of plate 150 (see, e.g. FIG. 5). The second section 204 also includes first and second configured arms 214, 216. The first configured arm 214 is configured and/or dimensioned in like manner to the channel 209 and thus to be slidingly receivable into the configured channel 209. The second configured arm 216 is also configured and/or dimensioned in like manner to the channel 210 and thus to be slidingly receivable into the configured channel 211. The arms 214, 216 are of a length to be fully received in the respective channel 209, 211 so the ends of the legs 208, 210 abut the ends of the arms 214, 216. In this manner, the dynamic 1-L plate 200 of FIG. 10 provides relative movement between the two sections or components 202, 204.

Figure 11:
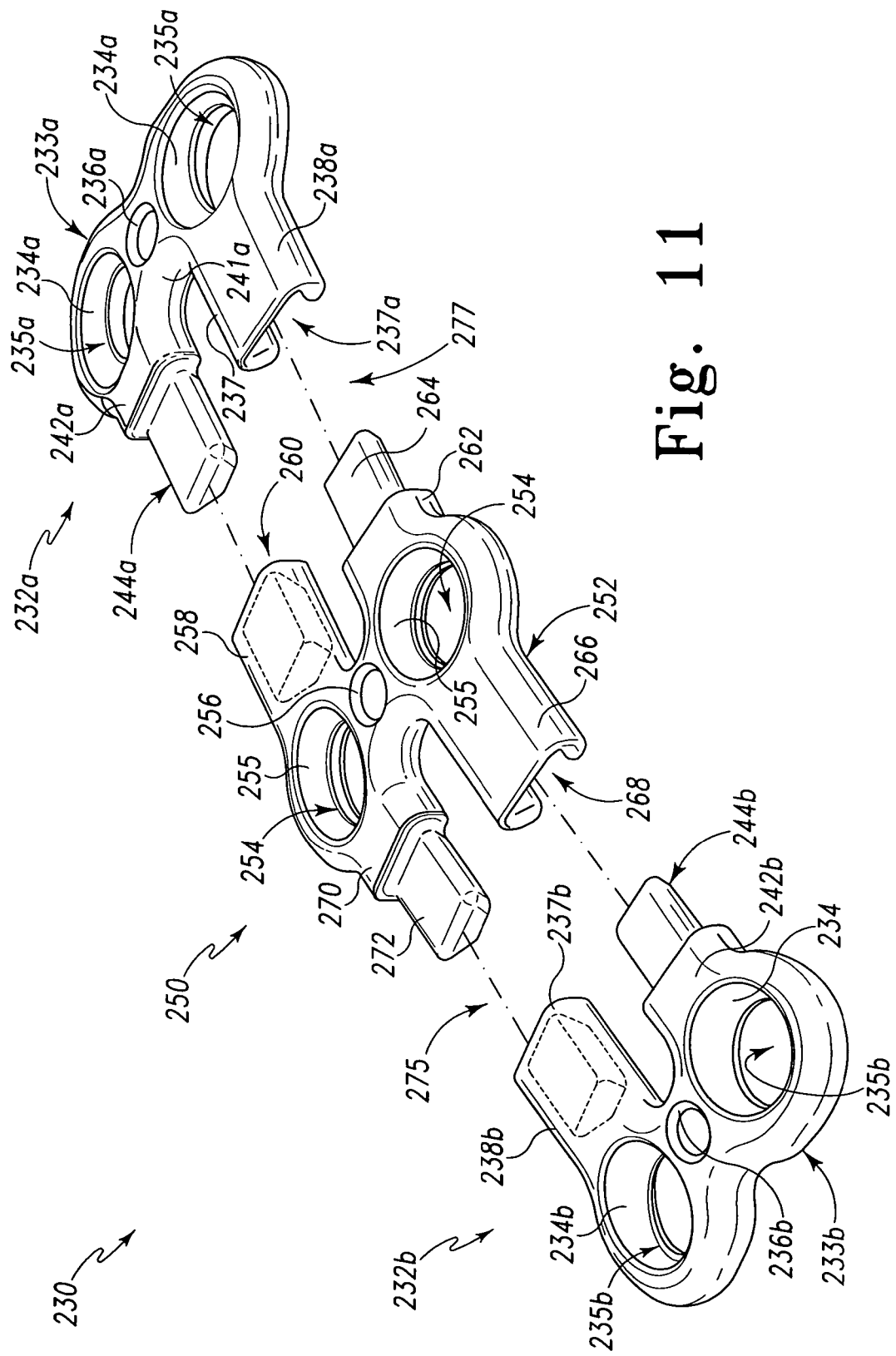
FIG. 11 is a perspective view of an exemplary embodiment of a two-level (2-L) dynamic bone fixation plate fashioned in accordance with the principles of the subject invention, the 2-L dynamic plate shown with each end plate component of the 2-L dynamic plate in exploded view relative to an intermediate plate component of the 2-L dynamic plate.

Referring to FIG. 11, there is depicted an exemplary embodiment of a dynamic two level (2-L) plate generally designated 230 formed in accordance with an aspect of the subject invention. The dynamic 2-L plate 230 is shown in exploded form to better illustrate the manner in which the dynamic plate is assembled, joined and/or is dynamic or dynamizes. This also illustrates how the middle plate component 250 may be used with itself to form n-levels of cervical plates with end components (i.e. two end plate components 232 for attachment to beginning and end vertebrae, and n middle plate components 250 defining the n-levels for attachment to n number of middle vertebrae), and moreover with each level providing dynamization (internally dynamizing). Thus, each internal or middle section is dynamizing as between themselves, not just the end plate components relative to a middle portion. The dynamic 1-L plate 200 is characterized by a first section 202 and a second section 204 that when assembled or together provides an opening, void or window 117. The size of the opening 117 is variable depending on the position of the two sections 202, 204 relative to one another. Each section 202, 204 defines a U-shape or portion that slidingly mates with one another to provide dynamization when attached. This sliding motion is unconstrained such that it smoothly transitions between various positions without ratchets or the like. The sections 202, 204 each provide a fastening portion, one for each vertebra. The window 217 exposes an area between the vertebrae. It should be appreciated that the configuration of such mating may be modified and/or deviate from that shown.

As such, the dynamic plate 230 has extended windows or openings formed by the dual pillar structure and, more particularly, has two windows formed by two dual pillar structures. The dynamic plate 230 is a two level (2-L) plate that is composed of three components which are shown in exploded view relative to one another in FIG. 11. The plate 230 is formed of a middle plate component 250 and two end plate components 232a and 232b. The two end plate components 232a and 232b are identical. A 180° reversal of an end component 232, in conjunction with the configuration of the middle component 250, allows the dynamic 2-L plate to utilize only two different pieces. Therefore, kits to provide n-level plates would come with two end plate components, and a plurality of middle plate components.

End component 232a is defined by a body 233a having bone screw bores 235a and configured ledges 234a such as described above. A retention bore 236a for a locking clip 170 or cover plate boss is provided between the two bone screw bores. The body 233a defines a first leg 238a having a configured channel or cutout 237a therein. The shape of the channel 237a provides lateral and up/down stability to a joining or mating piece of the middle component 250. Thus, the configuration of the channel may be changed as appropriate under the present principles. In this particular form, the channel 237a is configured akin to a dovetail. A second leg 244a of the body 233a is configured akin to the channel 237a dovetail. It should be observed that the end components 232a and 232b may be joined or assembled into a dynamic 1L plate without the use of the middle component 250 since the leg 244b (identical to leg 244a) will be received in leg channel 237a while the leg 244a will be received in leg channel 237b (identical to leg channel 237a).

The end component 234b is defined by a body 233b having bone screw bores 235b and configured ledges 234b such as described above. A retention bore 236b for a retention clip or cover boss is provided between the two bone screw bores. The body 233b defines a first leg 238b having a configured channel or cutout 237b therein. The shape of the channel 237b provides lateral and up/down stability to ajoining or mating piece of the middle component 250. Thus, the configuration of the channel may be changed as appropriate under the present principles. In this particular form, the channel 237b is configured akin to a dovetail. A second leg 244b of the body 233b is configured akin to the channel 237b dovetail.

The middle or expansion component 250 is defined by a body 252 having two bone screw bores 254 having head seats 255, and a boss bore 256. The body 252 also includes a first leg 258 having a configured channel 260 therein. The channel 260 receives the configured leg 244a of the section 232a (or flange 272 of another expansion component) and is thus configured appropriately. A second leg 262 of the body 252 includes a configured flange 264 that is configured to be received in the channel 237a of the section 230 (or a channel 268 of another expansion component) and is thus configured appropriately. A third leg 270 includes the configured flange 272 receivable in the channel 237b of the section 232b (or in the channel 260 of another expansion component). A fourth leg 266 of the body 252 includes the channel 268 that receives the configured flange 244 of the section 230 or the flange 264 of another expansion device. This structure and/or interrelationship of the middle component 250 to itself and to the end components 232, provides the ability to assemble N-level, dynamic plates. The 2-L dynamic plate 230, when assembled, defines first and second windows, voids or openings 275, 277 between the middle component 250 and each end component 232. The legs and flanges when assembled each have the same cross-section. The truncated triangle cross-section provides loading stability. This is an example of one embodiment. Other embodiments may be fashioned and utilized.

Figure 12:
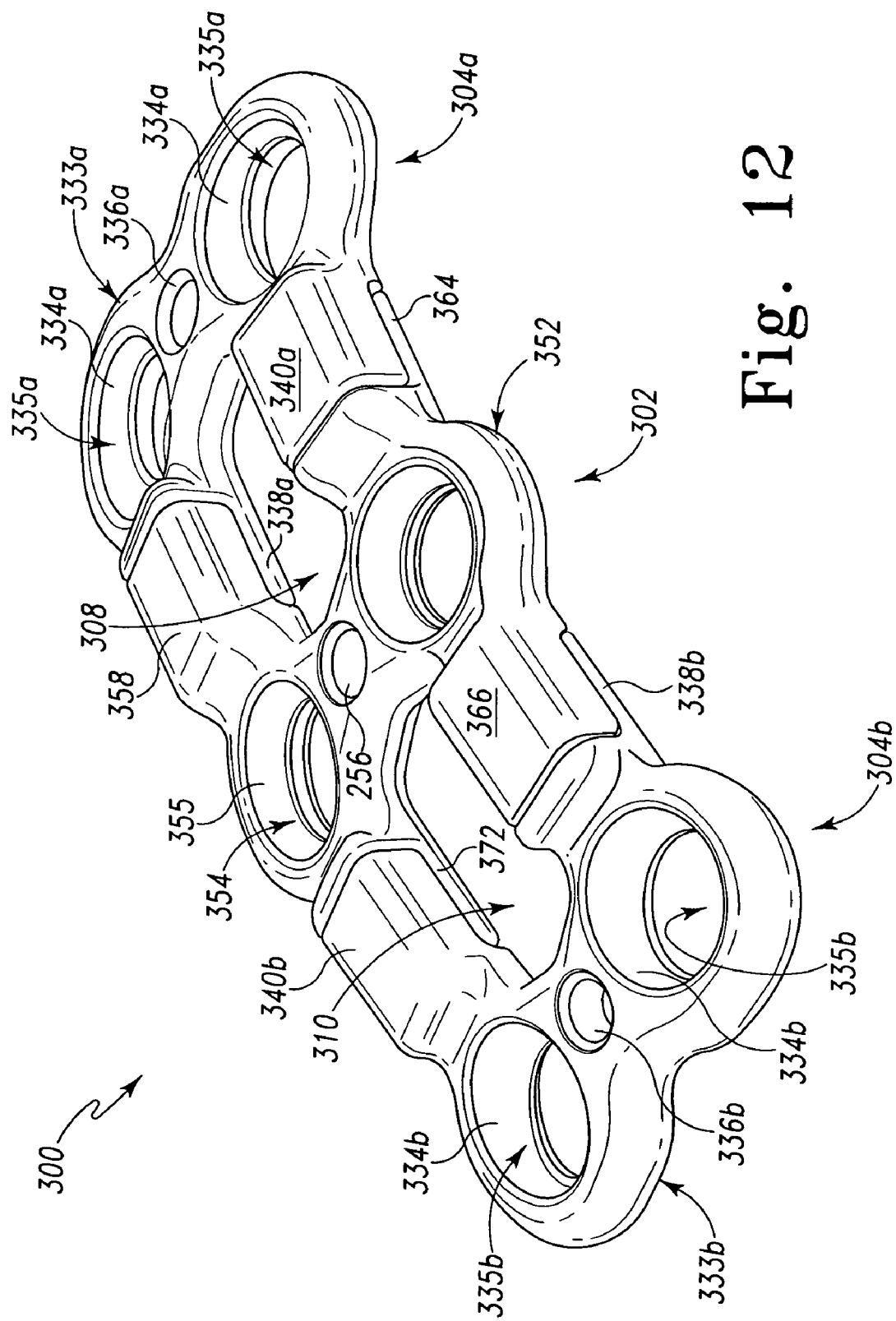
FIG. 12 is a perspective view of an exemplary embodiment of another 2-L dynamic bone fixation plate fashioned in accordance with the principles of the subject invention, the 2-L dynamic plate shown with end plate components thereof in an exploded position relative to an intermediate or extension plate component thereof in accordance with the principles of the subject invention.

FIG. 12 depicts another exemplary embodiment of a dynamic two-level cervical plate, generally designated 300, that is a variation of the dynamic two-level cervical plate 230 but which incorporates the features and/or functions of the plate 230. As such, the 2-L plate 300 has components that can be assembled to form a 1-L plate or an n-level plate. The plate 300 is formed of a middle component 302 and first and second identical end components 304a, 304b. Like plate 230, the dynamic plate 300 has extended windows or openings formed by dual pillar structures. The dynamic plate 300 is a two level (2-L) plate that is composed of three components which are shown assembled in FIG. 11. The plate 300 is formed of a middle plate component 302 and two end plate components 304a and 304b. The two end plate components 304a and 304b are identical. A 180° reversal of an end component 304, in conjunction with the configuration of the middle component 302, allows the dynamic 2-L plate to utilize only two different pieces.

End components 304a/b is defined by a body 333a/b having bone screw bores 335a/b and configured ledges 334a/b such as described above. A retention bore 336a/b for a retention clip or cover boss is provided between the two bone screw bores. The body 333a/b defines a first leg 338a/b having a configured mating structure thereon. The body 333a/b also defines a thickened second let 340a/b that has a channel for receiving a like configured leg portion of the middle component 302, the shape of which provides lateral and up/down stability to a joining or mating piece of the middle component 302. Thus, the configuration of the channel may be changed as appropriate under the present principles. It should be observed that the end components 304a and 304b may be joined or assembled into a dynamic 1 L plate without the use of the middle component 302

The middle or expansion component 302 is defined by a body 352 having two bone screw bores 354 having head seats 355, and a boss bore 356. The body 352 also includes a first thickened leg 358 having a channel therein that is configured to receive the configured leg 338a of the end component 304a (or flange 366 of another middle component 350) and is thus configured appropriately. A second leg 364 of the body 352 includes a flange that is configured to be received in the channel structure 340a of the end component 304a (or a channel 366 of another middle component) and is thus configured appropriately. A third leg 372 includes configured flange receivable in the channel structure 340b of the end section 232b (or in the channel of another middle component). A fourth leg 366 of the body 352 includes a channel structure that receives the configured flange 338b of the end component 304b or the flange of another middle component. This structure and/or interrelationship of the middle component 302 to itself and to the end components 304, provides the ability to assemble N-level, dynamic plates. The 2-L dynamic plate 300, when assembled, defines first and second windows, voids or openings 308, 310 between the middle component 302 and each end component 304. The legs and flanges when assembled each have the same cross-section. The legs and flanges when assembled each have the same cross-section.

The various dynamic plates of the present invention are assembled from a number of end and middle components depending on the desired plate level. The various components are slidingly interconnected to one another. It should be appreciated that once assembled, the plate components, while slidable with respect to each other, have a disassembly stop or constraining mechanism or device such that the plate components will not disassemble once assembled. The disassembly constraining mechanism constrains or limits the length of travel of the leg assemblies (slidingly connected legs of the plate components) of the two plate components relative to one another in a disassembled direction of travel.

Figure 13:
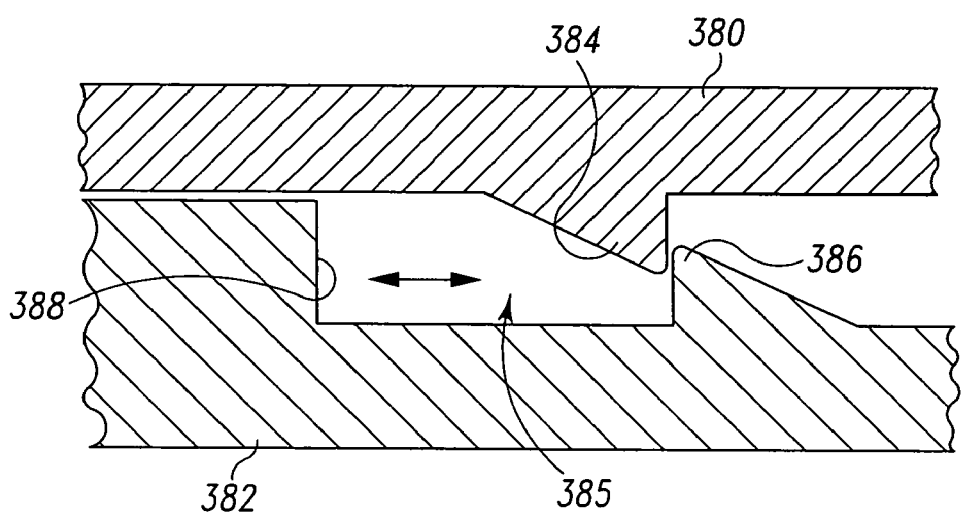
FIG. 13 is an enlarged sectional view of an exemplary constraining mechanism that may be utilized in the present dynamic plates.

To this end and referring to FIG. 13, there is depicted an exemplary disassembly constraining mechanism for the present dynamic plate components. Particularly, FIG. 13 illustrates an enlarged portion of two slidingly interconnected legs 380, 382 of any two assembled dynamic plate components according to the principles of the present invention. Leg 380 may be a configured leg with a channel or groove, while the leg 382 is a configured leg with a flange, or vice versa such as described herein. When referring to FIG. 13, however, the arm 380 will arbitrarily considered a configured channel arm and the arm 382 necessarily considered the configured flange arm. It should also be appreciated that distances and lengths are not necessarily to scale and/or in proportion with one another.

The channeled arm 380 has a detent 384 within the groove (the underside per FIG. 13) of the arm 380. The detent 384 extends a distance from the groove surface into the arm 385 and is preferably, but not necessarily, in the form of a right triangle having a sharp to rounded apex. The flanged arm 382 includes a notched or cutout area or portion 385 bounded by a ledge 388. A detent 386, again preferably, but not necessarily in the form of a right triangle having a sharp to rounded apex, is situated within the area 385.

During assembly, the detent 386 is to the left of detent 384. While the heights of the detents are such that the apex of each detent extends beyond the apex of the other detent, as the two detents 384, 386 meet their angled or ramped surfaces meet. Continued travel allows the ramps to slide relative to another. The small overlap in detent height thus allows the detent 384 to reside in area 385 once full assembly has taken place. In one direction of travel, the detent 384 will contact ledge 388, while in the other direction the difference in detent height creates a stop. Of course, other types of stop mechanisms may be employed that allow assembly but prevents disassembly or makes disassembly extremely difficult.

Figure 14:
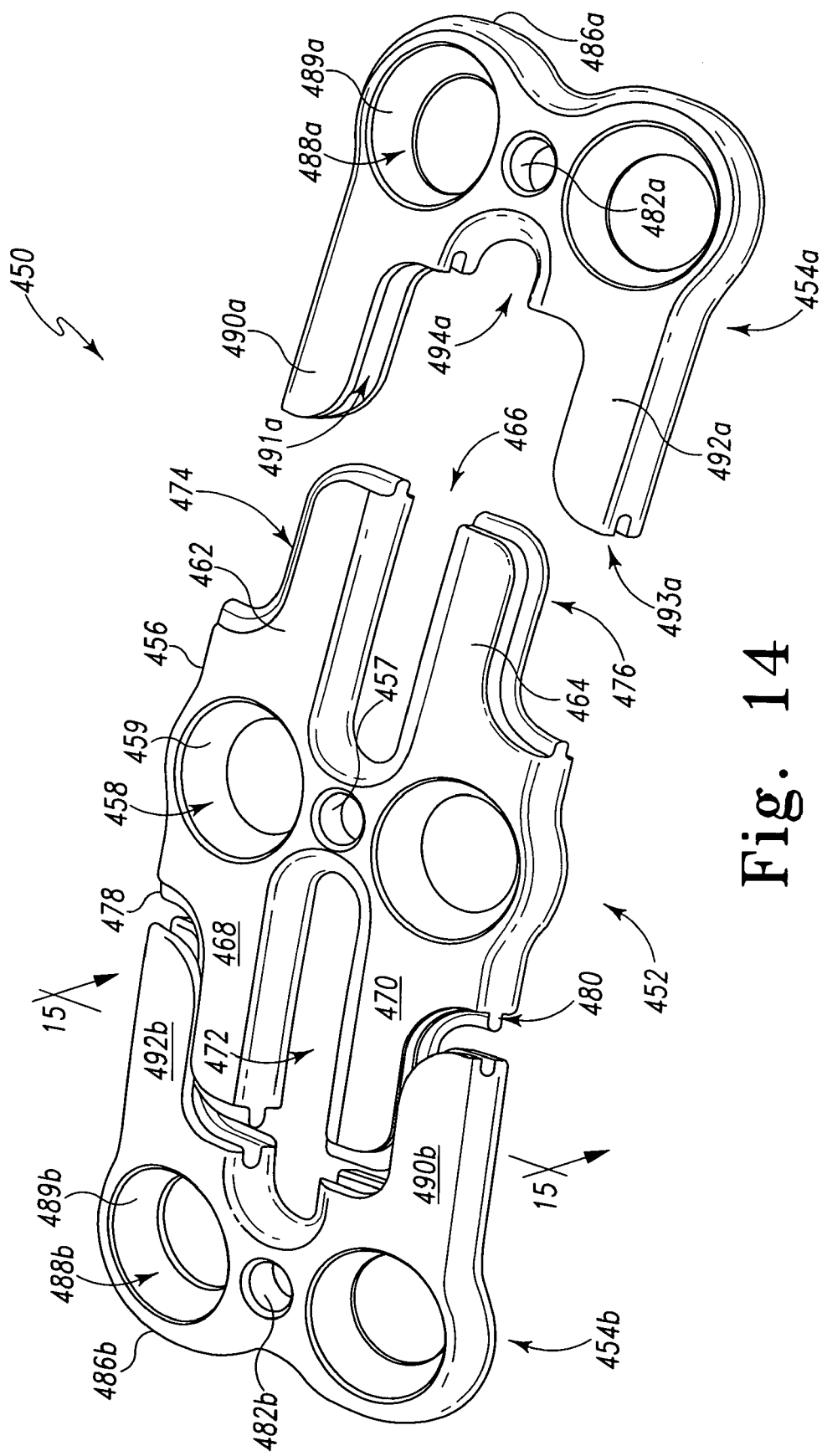
FIG. 14 is a perspective view of an exemplary embodiment of another 2-L dynamic cervical bone fixation plate fashioned in accordance with the principles of the subject invention, the 2-L dynamic plate shown with end plate components thereof in an exploded position relative to an intermediate or extension plate component thereof in accordance with the principles of the subject invention.

FIG. 14 depicts an exemplary embodiment of another unconstrained 2-L dynamic cervical bone plate, generally designated 450, configured, adapted and/or operable to attach to three adjacent vertebrae such as for the fusion of the three vertebrae in like manner to the other 2-L plates described herein. The plate 450 thus includes three bone screw attachment or mounting sections or portions defined in end plate components 454a and 454b, and middle plate component 452, with one bone screw mounting portion for each vertebra. The 2-L dynamic cervical bone plate 450 therefore includes the middle, extension, or dynamizing plate component 452, and the first and second end plate components 454a and 454b. The first and second end plate components are preferably and so numbered as, but not necessarily, identical.

The middle component 452 is configured to present the same face when rotated about the plane of the paper (i.e. rotatable 180° and still present the same configuration) and/or symmetric about a top to bottom plane through the bone screw bores 458. In this manner a single configuration of end plate component 454 is used at both ends of the middle component 450. The middle plate component 450 allows one-plane movement ('dynamization') relative to both end plate components 454a, 454b when mounted, or between each end plate component 454a, 454b and the middle plate component 452.

Figure 16:
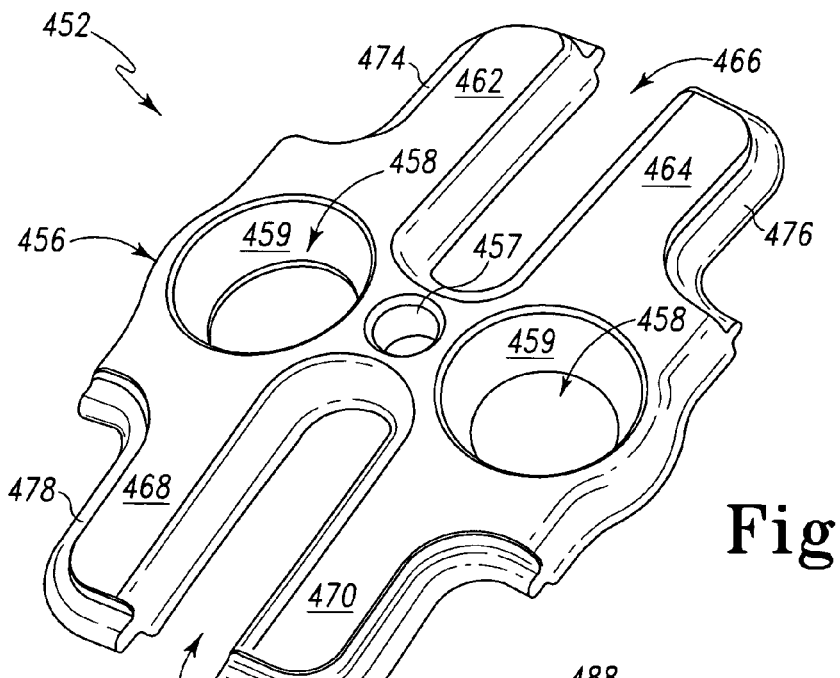
FIG. 16 is a perspective view of the intermediate or extension plate component of the 2-L dynamic plate of FIG. 14.

Referring additionally to FIG. 16, the middle plate component 452 is characterized by a body 456 defining two bone screw bores 458 and a boss bore 457. Each bone screw bore 458 is sized to allow the shank of a bone screw to pass through the bore 458. The bone screw bore, however, includes an annular and truncated conic section ledge 459 that extends radially inwardly to prevent the head of the bone screw to pass through the bore 458. The boss bore 457 is sized to receive a boss of a clip, cover or the like as described above.

The middle plate component 452 has two legs or flanges, 462 and 464 extending from one end of the body 456. The two legs 462, 464 are spaced apart and parallel, but preferably, but not necessarily, slightly curved downwardly (as per FIG. 16) from a middle plane defined between the two centers of the bone screw bores 458. The legs 462 and 464 also define a cutout 466 that forms a portion of an opening or window between the middle plate component 452 and an end plate component 454a. The edge of the leg 462 has a ridge 474. Likewise, the edge of the leg 464 has a ridge 476. Each ridge 474, 476 is preferably, but not necessarily, centered between a top surface of the middle plate component 452 and a bottom surface of the middle plate component 452 (i.e. thickness).

The middle plate component 452 also has two more legs or flanges, 468 and 470 extending from another end of the body 456, opposite the legs 462, 464. The two legs 468, 470 are spaced apart and parallel, but preferably, but not necessarily, slightly curved downwardly (as per FIG. 16) from a middle plane defined between the two centers of the bone screw bores 458. The legs 468 and 470 also define a cutout 472 that forms a portion of an opening or window between the middle plate component 452 and an end plate component 454b. The edge of the leg 468 has a ridge 478. Likewise, the edge of the leg 470 has a ridge 480. Each ridge 478, 480 is preferably, but not necessarily, centered between a top surface of the middle plate component 452 and a bottom surface of the middle plate component 452 (i.e. thickness). As described below, the ridges are designed to be received in a corresponding groove, channel or notch of the legs of the end plate component. This is termed a tongue and groove configuration.

Figure 17:
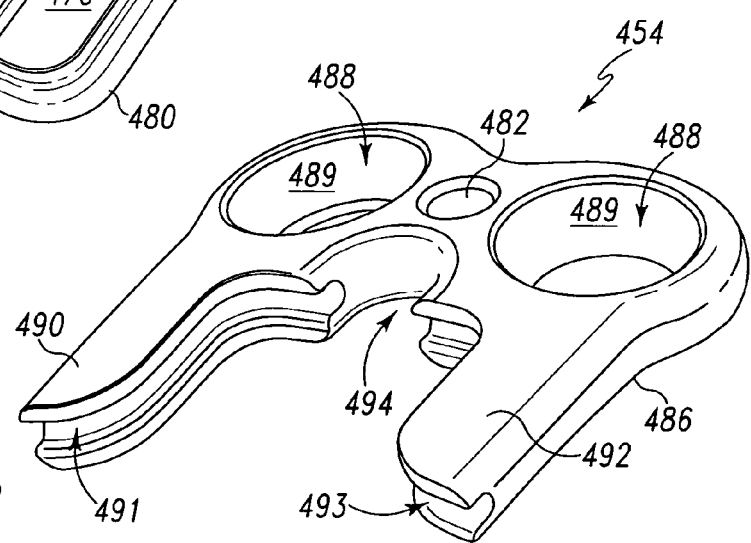
FIG. 17 is a perspective view of the end plate component of the 2-L dynamic plate of FIG. 14.

With respect to the end plate component, attention is drawn to FIG. 17 in addition to FIG. 14, wherein the end plate component 454, representing both end plate components 454a and 454b, is depicted. It should be appreciated that the end plate component 454 is used as an end plate component for both ends of the plate 450. As such, the end plate component 454 is rotatable 180° (around the plane of the paper) and able to maintain the same configuration. The end plate component 454 has a body 486 having two bone screw bores 488. Each bone screw bore 488 is sized to allow the shank of a bone screw to pass through the bore 488. The bone screw bore, however, includes an annular and truncated conic section ledge 489 that extends radially inwardly to prevent the head of the bone screw to pass through the bore 488. The boss bore 488 is sized to receive a boss of a clip, cover or the like as described above.

The middle plate component 454 has two legs or flanges, 490 and 492 extending from one end of the body 486. The two legs 490, 492 are spaced apart and parallel, but preferably, but not necessarily, slightly curved upwardly (as per FIG. 16) from the two centers of the bone screw bores 488. A cutout or notch 494 forms a portion of an opening or window between a cutout 466 or 472 of the middle plate component 452 and the end plate component 454. The edge of the leg 490 has a groove or channel 491. Likewise, the edge of the leg 492 has a groove or channel 493. Each groove 491, 493 is preferably, but not necessarily, centered between a top surface of the end plate component 454 and a bottom surface of the end plate component 454 (i.e. thickness). As well, the grooves 491 and 493 are sized to receive the ridges 474, 476 or 478, 480.

Figure 15:
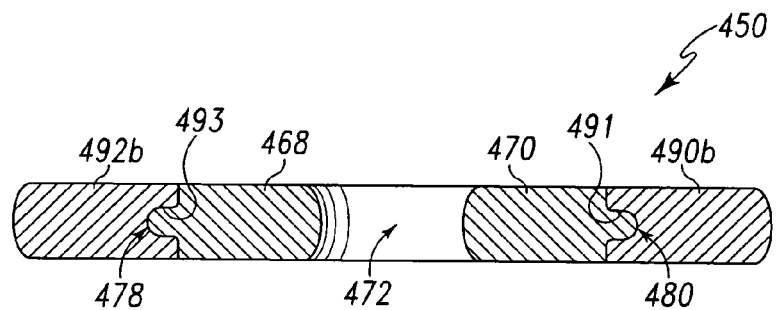
FIG. 15 is a sectional view of the 2-L dynamic bone fixation plate of FIG. 14 taken along line 14-14 thereof, particularly showing the interrelationship of the leg structures of the end and intermediate components.

This is particularly illustrated in FIG. 15 and attention is drawn thereto. FIG. 15 depicts a sectional view of the plate 450 taken along line 15-15 of FIG. 14. FIG. 15 particularly illustrates the manner of how the end plate component slidingly mates with the middle plate component. The ridge 480 of the leg 470 of the middle plate component is received in the groove 491 of the leg 490b of the end plate component. Likewise, the ridge 478 of the leg 468 of the middle plate component is received in the groove 493 of the leg 492b of the end plate component. This configuration allows one or more plates to slide relative to one another but provide lateral and up/down stability throughout the dynamizing length. The plate 450 is internally dynamizing in that the end components each can move independently of each other but both with respect to the middle component. Moreover, thickness of the plate remains the same or constant throughout its length. Of course, the ridges and grooves may be reversed. Other interlocking structures such as a dovetail or modified dove tail or dove tail type configuration, may also be used in accordance with the present principles.

It should be appreciated from the above that while the legs or projections of the 2-L dynamic plate 450 are in sliding interconnectivity when assembled in like manner to the previously discussed 2-L dynamic plates of the present invention, the manner of such sliding interconnectivity is different. The present dynamic plate 450 utilizes an extended or modified tongue and groove configuration on rim portions of the various projections.

Figure 18:
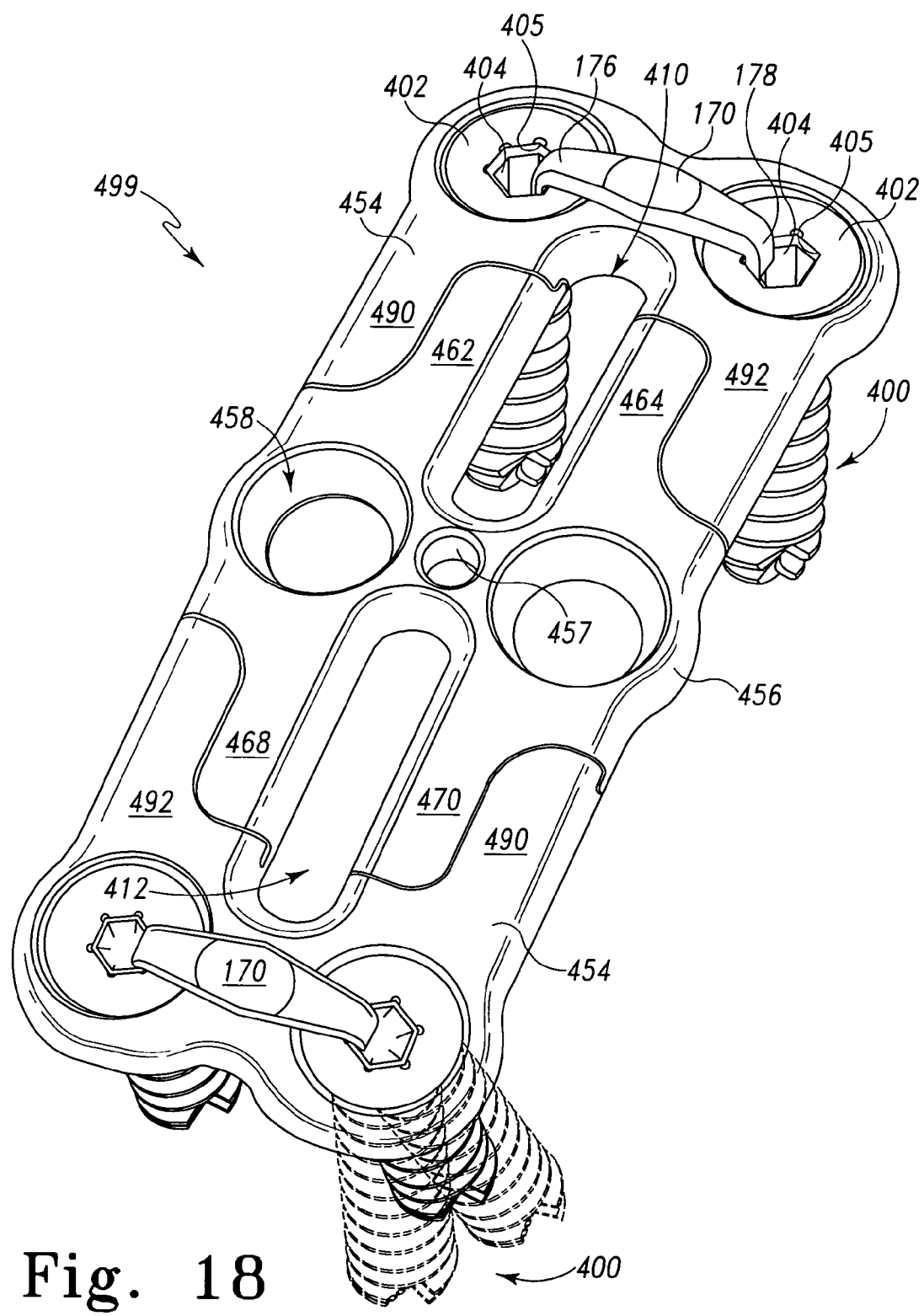
FIG. 18 is a perspective view of another exemplary 2-L dynamic plate construct utilizing the 2-L dynamic plate of FIG. 14.

FIG. 18 depicts an unconstrained 2-L dynamic cervical plate construct, generally designated 399 is shown utilizing the 2-L internally dynamizing cervical plate 450. Particularly, the construct 499 includes the plate 450, a plurality of bone screws 400, and a plurality of bone screw retainers such as clips 170. The windows 410 and 412 of the plate 450 are complete when the plate 450 is assembled. A bone screw labeled 400 is shown in various orientations representing the various orientations that a bone screw is able to achieve with the plate 450. Moreover, a clip 170 is shown attached to the end plate component 454 (via its boss bore) and spans a pair of bone screws. Particularly the flange 176 is received in polygon-shaped socket 404 of the screw head 402 of the top left bone screw, while the flange 178 is received in polygon-shaped socket 404 of the screw head 402 of the top right bone screw.

Figure 19:
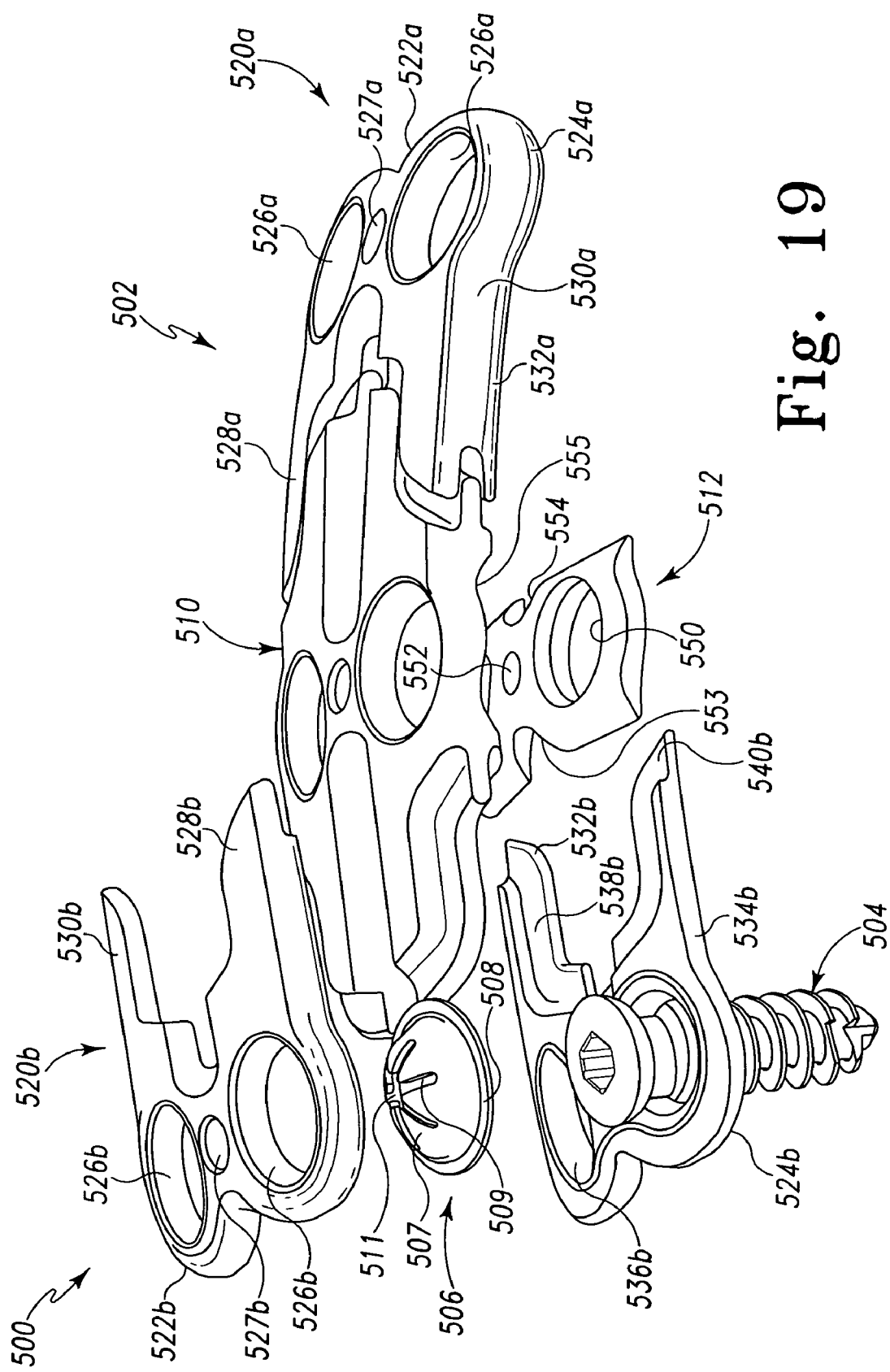
FIG. 19 is a perspective view of another exemplary 2-L dynamic plate construct and dynamic plate that is a variation of the 2-L dynamic plate of FIGS. 14-18, an end plate component thereof having two pieces shown in exploded view, the construct of FIG. 19 shown utilizing a screw capture device in accordance with the principles of the subject invention.
Figure 20:
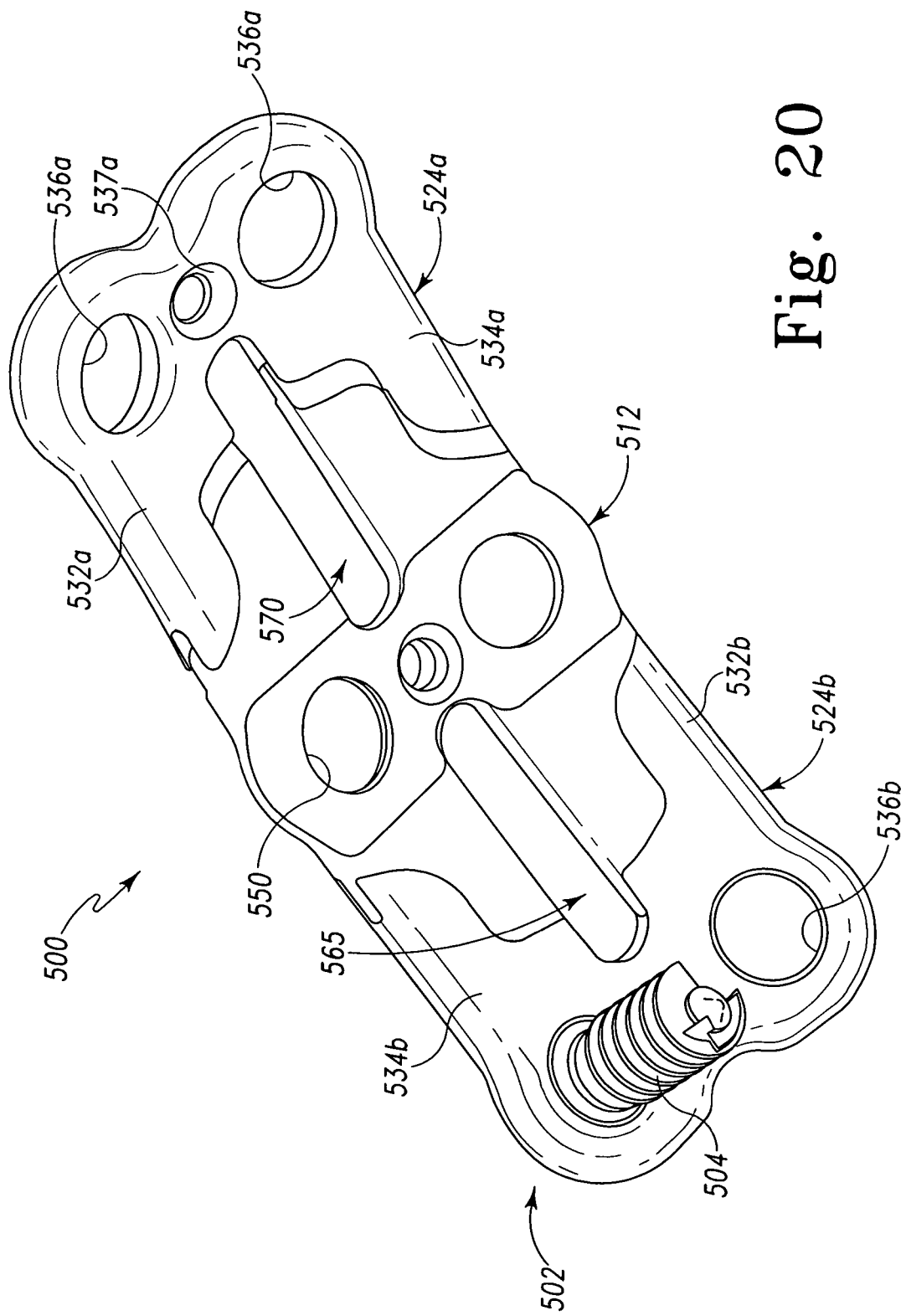
FIG. 20 is a bottom view of the 2-L dynamic plate construct of FIG. 19.

Referring now to FIGS. 19 and 20, there is depicted an unconstrained 2-L internally dynamizing (dynamic) cervical plate construct, generally designated 500. The construct 500 includes a 2-L a dynamic plate 502, one or more bone screws 504, and one or more screw capture devices 506. The dynamic plate 502, when assembled, is identical in configuration, function and features to the 2-L dynamic plate 350. The dynamic plate 502, however, utilizes a two-piece structure for the end components 520a, 520b, and includes a base plate 512 for the middle component 510. The middle component 510 is essentially the same as the middle component 356 of dynamic plate 350, except for a base plate component reception area 555 on the underside of the middle component 560. The base plate component 512 having two bone screw bores 550 that align with the bone screw bores of the middle plate component 510 and a boss bore 552 that align with the boss bore of the middle plate component 510. Moreover, the base plate component 512 includes two window notches 553 and 554. The window notches 553 and 554 form portions of the windows 565 and 570 when assembled (see FIG. 20).

While identical (thus 180° rotatable in the plane of the paper) end plate components 520a and 520b of the dynamic plate 502 have the same configuration, features and functions as the end plate components 354a and 354b, the end plate components 520a and 520b are assembled from two pieces rather than formed as one piece. Each end plate component 520a and 520b has an upper end plate component portion 522a and 522b and a lower end plate component portion 524a and 524b that join to form the respective end plate components 520a and 520b. The upper and lower end plate components 522 and 524 are essentially a split or half of the like end plate component 354 of the dynamic plate 350.

As such, and referring to the end plate component 520b, the upper end plate component portion 522b includes bone screw bores 525b and two extending legs 528b and 530b. The legs 528b and 530b are spaced in a U-shape to define the window 565 when assembled. While not discernable in FIG. 19, each leg 528b and 530b is configured to have a groove on one side thereof that cooperate with grooves 538b and 540b of the legs 534b and 532b of the lower end plate component portion 524b to form the central groove as shown with respect to the end plate component 354 of the dynamic plate 350. A boss bore portion 527b cooperates with the lower portion 537b (see FIG. 20).

The construct 500 is shown with a bone screw capture or releasable bone screw locking (anti-rotation/backout) device 506. It should be appreciated that the construct 500 preferably includes a screw capture device 506 for each bone screw 504/bone screw bore of the dynamic plate 502. The screw capture device 506 is characterized by a body 507 that may be formed of a suitable biocompatible polymer or metal. The body 507 is dome shaped having an annular rim 508. The domed body 506 includes a plurality of slits or slots from a central opening 511.

The screw capture device 506 is situated and captured between the end plate component portions 522 and 524 and any number of middle components 510 and 512. Particularly, the rim 508 is constrained by the ledge of the bone screw bores. The inner surface of the body 506 compresses against the head of the bone screw to provide anti-backing or anti-rotation of the bone screw 504 once installed.

Figure 21:
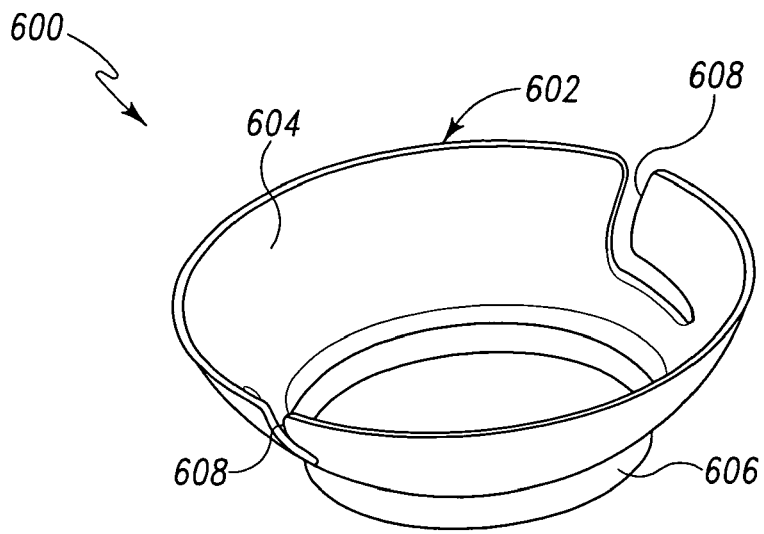
FIG. 21 is a perspective view of a bone screw locking device for use with the present cervical plates in accordance with the principles of the present invention.

Referring to FIG. 21, there is depicted an embodiment of another bone screw releasable locking, anti-backout and/or anti-rotation device generally designated 600. The bone screw anti-backout device 600 is characterized by a body 602 that may be formed of a suitable biocompatible polymer or metal. The body 602 has a generally annular dish or cup shaped portion 604 that extends from an annular base 606. The annular dish-shaped portion 604 is shaped in like manner to the undersurface of a bone screw head and thus upwardly and outwardly flares from the base 606. The annular dish-shaped portion 604 further includes one or more (two of which are shown) configured slots 608. The slots are configured as a vertical portion extending from the upper rim of the annular dish-shaped portion 604 with a connected annular horizontal portion. This structure binds against the screw head to reduce and/or prevent backout of the bone screw.

Figure 22:
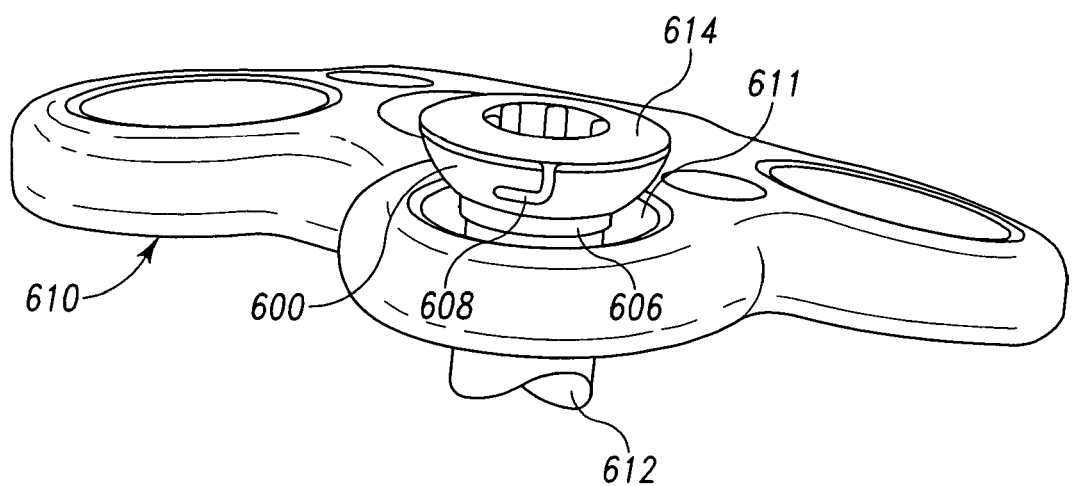
FIG. 22 is a side perspective view of the bone screw locking device of FIG. 21 shown utilized on a bone screw

Referring to FIG. 22, the bone screw anti-backout/rotation device 600 is shown in use. Particularly, a cervical plate component 610 is depicted having bone screw bores 611. A bone screw 612 is shown extending through a bone screw bore 611. A bone screw anti-backout device 600 is shown situated around the undersurface of the head 614 of the bone screw 612. Bone screw anti-backout device 600 is thus situated between the undersurface of the bone screw head and the ledge within the bone screw bore. The configured slots 608 allow rotation of the screw in one direction (installation) but aids in preventing rotation of the screw in the other direction (backing out).

Figure 23:
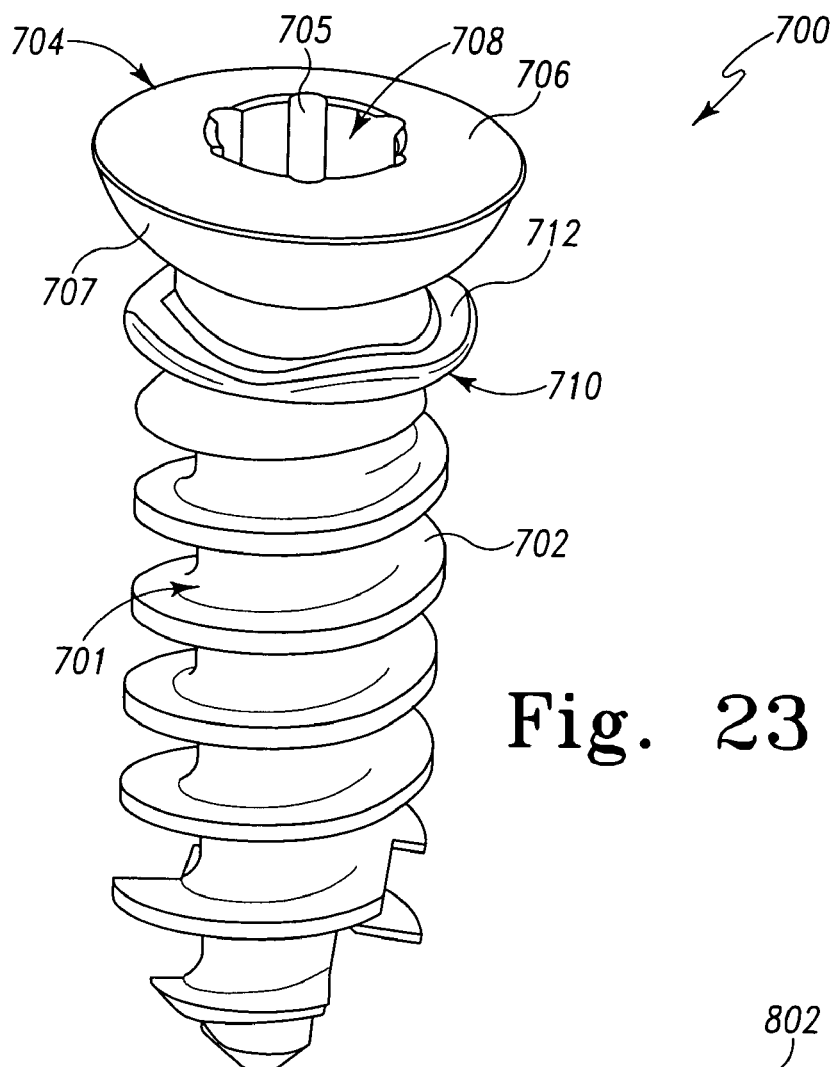
FIG. 23 is perspective view of an exemplary bone screw fashioned in accordance with an aspect of the subject invention, particularly showing its anti-backout surface.

Referring to FIG. 23, there is depicted a bone screw, generally designated 700 having an integral anti-backout feature that cooperates with an integral anti-backout feature of a bone screw bore. The bone screw 700 includes a typical threaded shank 702 and typical head 704. The head 704 includes an upper surface 706 in which is disposed a lobed, polygon socket 708. The bone screw 700, however, includes an annular, radially extending rim 710 that is disposed on the shank 702 a distance from the undersurface 707 of the screw head 704 but above the threads of the shank 702. The rim 710 includes a waved surface 712 on the upper side thereof, the waved or wavy surface extending about the shank 702.

Figure 24:
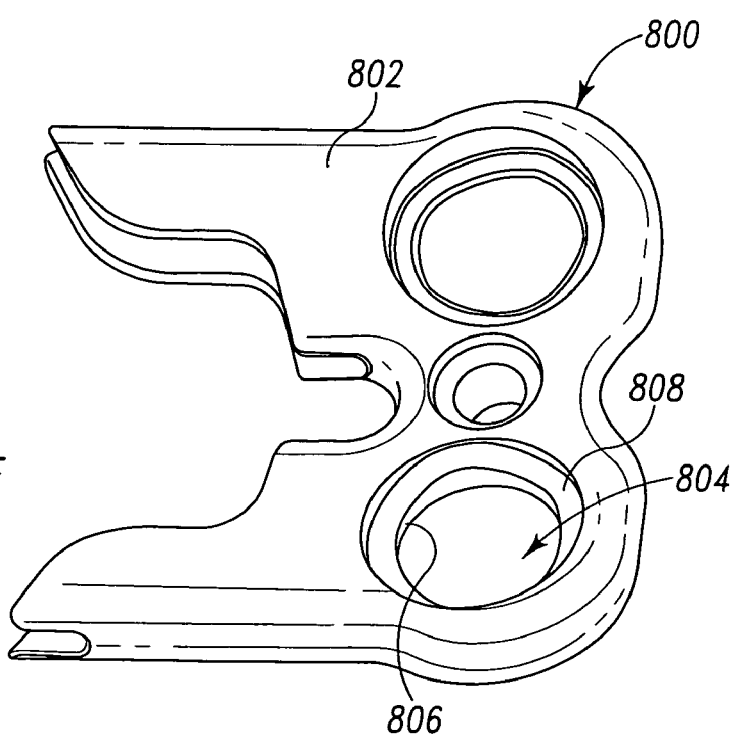
FIG. 24 is a perspective view of an enlarged end plate component particularly showing an anti-backout surface associated with a bone screw bore of the end plate component for use in conjunction with the bone screw of FIG. 23, in accordance with an aspect of the subject invention.

As indicated above, the integral anti-backout feature of the bone screw 700 is used in conjunction with an integral anti-backout feature of a bone screw bore. As such, attention is drawn to FIG. 24, which depicts an exemplary embodiment of an end plate component, generally designated 800. Particularly the undersurface 802 of the end plate component 800 is shown. A bone screw bore 804, representing all bone screw bores 804, includes a waved or wavy surface 808 defined on the undersurface of the bone screw bore ledge 806. The manner of co-action between the two integral anti-backout features, will be described with reference to FIG. 25.

Figure 25:
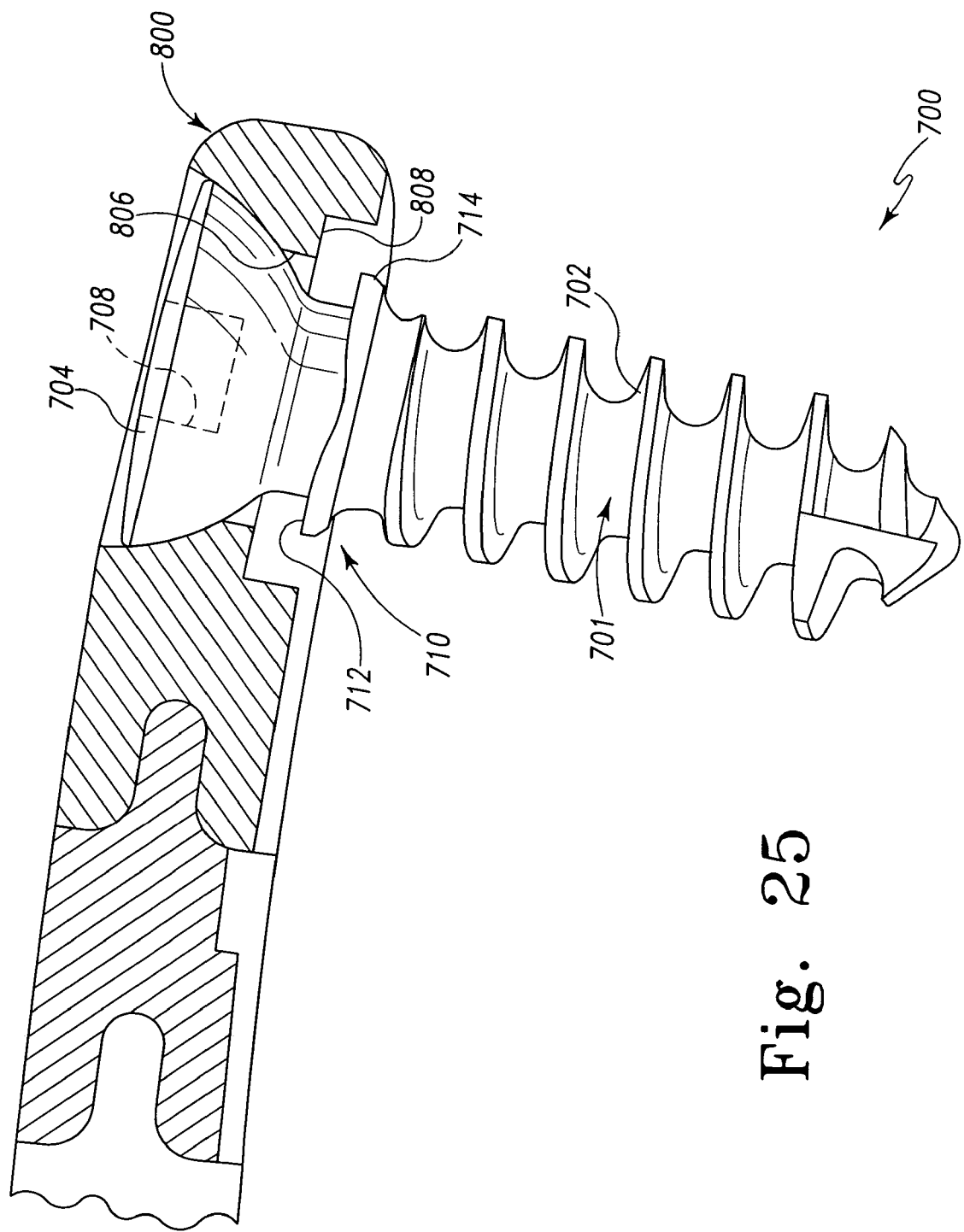
FIG. 25 is an enlarged, sectional side view of the end plate of FIG. 24 utilizing the bone screw of FIG. 23.

FIG. 25 shows a sectional view of the end plate component 800 with the bone screw 700 extending therethrough as it would after mounting of the plate. Once the rim 710 has been pushed beyond the screw bore ledge 806 because of the curved under surface 714 of the rim 710, upward rotational movement of the bone screw 700 makes the wavy surface 712 contact the wavy surface 808. The waved surfaces mesh not allowing further backing rotation of the screw. The bone screw, however, may be removed using high RPM and under head force.

Figure 26:
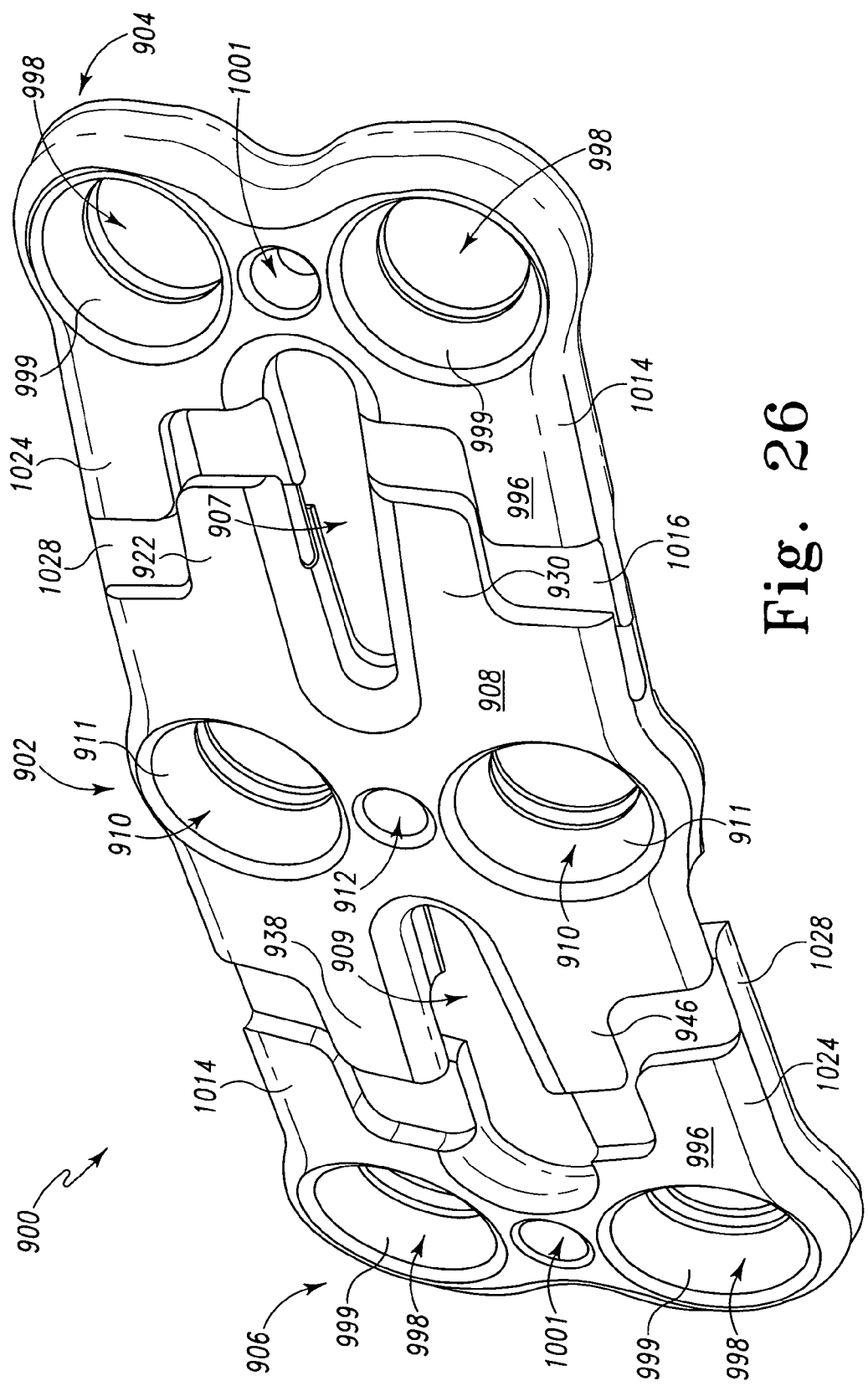
FIG. 26 is a perspective view of another exemplary embodiment of another exemplary 2-L dynamic cervical bone fixation plate fashioned in accordance with the principles of the subject invention, the 2-L dynamic plate shown with end plate components thereof in an exploded position relative to an intermediate or extension plate component thereof in accordance with the principles of the subject invention.

Referring now to FIG. 26 there is depicted an exemplary embodiment of another freely sliding or moving (unconstrained) 2-L dynamic cervical bone plate generally designated 900, configured, adapted and/or operable to attach (preferably, but not necessarily, in anterior aspect) to three adjacent vertebrae such as for the fusion of the three vertebrae in like manner to the other 2-L plates described herein. The plate 900 thus includes three components, a middle component 902, an end component 904 (arbitrarily a first end component 904) and an end component 906 (arbitrarily a second end component 906) each one of which includes bone screw bores for attaching the particular component to a vertebra. The components 902, 904, 906 are furthermore, in accordance with the present principles, configured for independent dynamizing (movement) between the middle component 902 and each end component 904 and 906. FIG. 26 illustrates this by depicting each end plate 904 and 906 in a different dynamization state (position relative to the middle component or in a position in its longitudinal length of travel relative to the middle component).

The middle component 902 is configured to present the same configuration when rotated in a plane defined by its body (i.e. rotatable 180° and still present the same configuration) and/or symmetric about a top to bottom plane through its bone screw bores 910. The end components 904 and 906 are configured to be received for sliding engagement with configured ends of the middle component 902 and, more particularly, for sliding engagement for assembly of the end component (904 or 906) to the middle component 902 and thereafter for sliding engagement or interconnectivity within a limited length of longitudinal travel between a fully closed (closed) position relative to the middle plate 902 and a fully open (open) position defined by ends of the components and configured stops that allow for sliding assembly of the components, but hinders disassembly. Since the middle component 902 presents the same configuration when rotated around end to end (in a plane defined by the body 908), at least the connection portions of the first and second end components 904, 906 are identical or nearly so. Preferably, however, and as shown in the figures, the first and second end components 904 and 906 are entirely identical. This allows the manufacture of only one configuration of end component (not including different sizes for different sizes of middle components).

In accordance with the principles of the subject invention, the plate 900 includes two graft windows 907, 909, one for each level. Each graft window 907 and 909 preferably, but not necessarily, has the same shape. Particularly, the graft window 907 extends essentially from the pair of bone screw bores 998 of the first end component 904 to the pair of bone screw bores 910 of the middle component 902. Likewise, the graft window 909 extends essentially from the pair of bone screw bores 998 of the second end component 906 to the pair of bone screw bores 910 of the middle component 902. Moreover, as discussed further below, the width of each window 907, 909 increases from an end of the window relative to the middle component 902 to and end of the window relative to the respective end component 904, 906. Of course, the windows 907, 909 may take other shapes.

Figure 29:
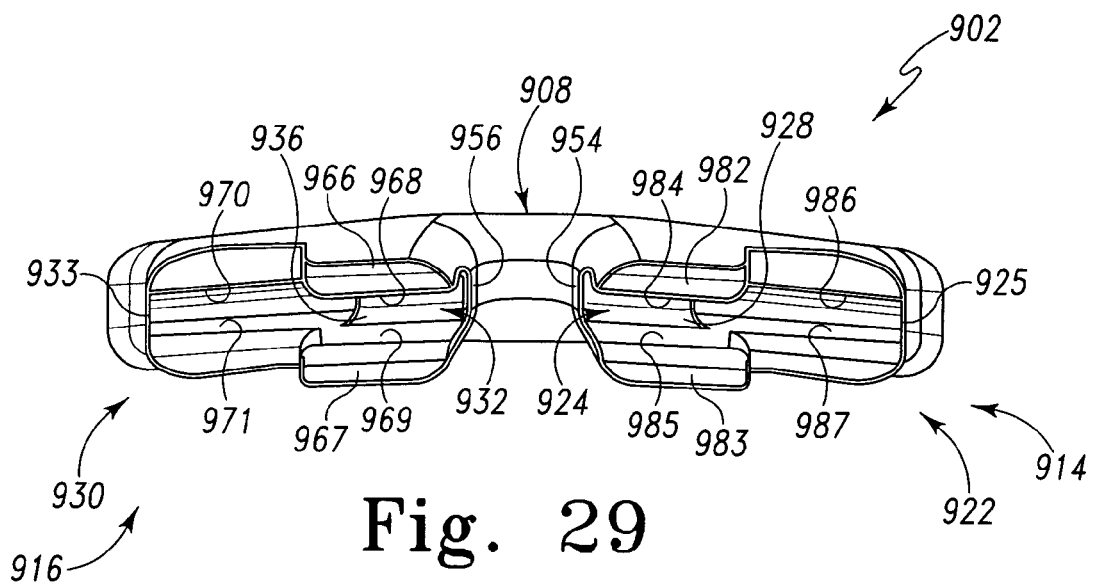
FIG. 29 is an end view of the 2-L dynamic plate of FIG. 27.
Figure 30:
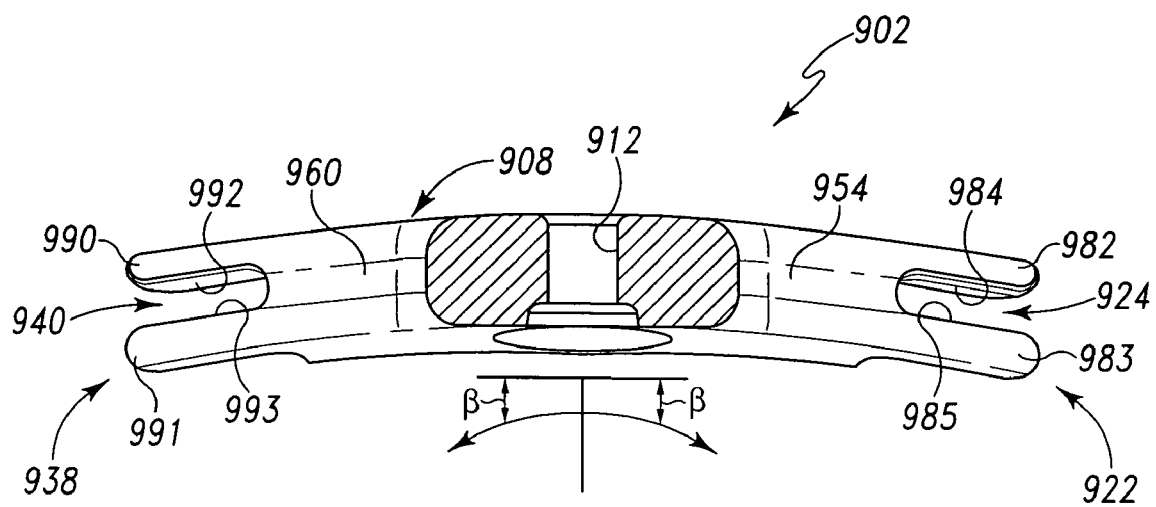
FIG. 30 is a sectional view of the 2-L dynamic plate of FIG. 27 taken along line 30-30 thereof.
Figure 31:
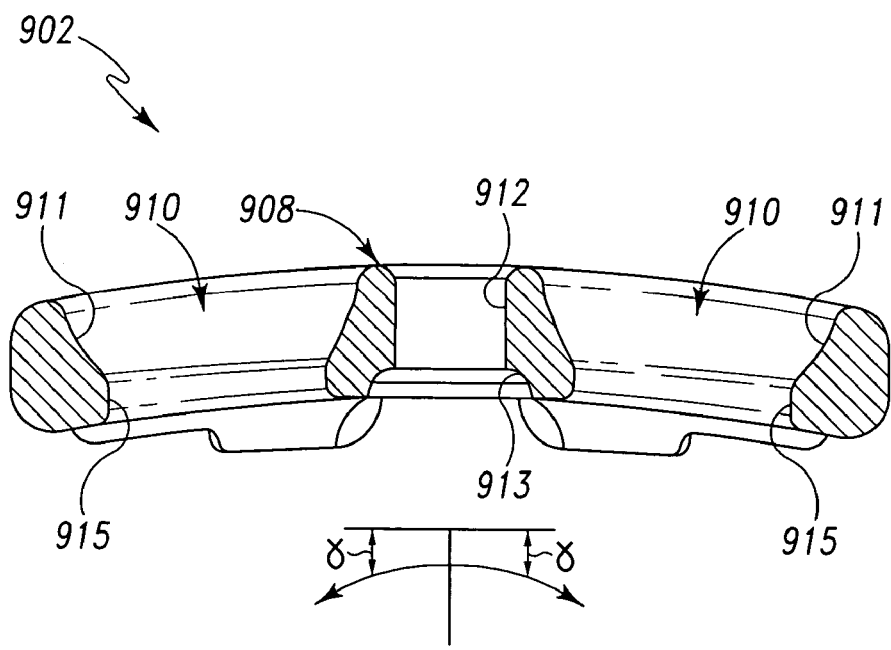
FIG. 31 is a sectional view of the 2-L dynamic plate of FIG. 27 taken along line 31-31 thereof.

Referring additionally to FIGS. 27-31, the middle or central component 902 is particularly illustrated. The middle component 902 is characterized by a body 908 that is formed of a biocompatible material such as titanium or a titanium alloy. The body 908 includes two bone screw bores 910 and a boss bore 912. The pair of bone screw bores 910 is preferably, but not necessarily, located in a longitudinal middle-line of the body 908. As well, the boss bore 912 is preferably, but not necessarily, located between the pair of bone screw bores 910 in the center of the body 908. Each bone screw bore 910 is sized to allow the shank of a bone screw to pass through the bore 910. Each bone screw bore 910 includes an annular and truncated dish shaped ledge 911 that extends radially inwardly to prevent the head of the bone screw to pass through the bore 910. As best seen in FIG. 31, each bone screw bore 910 also includes a radiused rim 915. The boss bore 912 is configured to receive a boss of a bone screw releasable locking mechanism, clip, cover or the like as described above.

The middle component 902 defines four lateral sides or side portions 914, 916, 918 and 920, with side portions 914 and 916 extending from one longitudinal end of the body 908 and side portions 918 and 920 extending from another longitudinal end of the body 908. The side portions 914 and 918 are diametrically opposed, while side portions 916 and 920 are diametrically opposed. Each side portion 914, 916, 918 and 920 is formed with a configured connection and/or reception interface portion or section 924, 932, 940 and 948, respectively, formed as a configured groove or channel within a respective side of the body 908. The side portions 914 and 916 define a connection and/or reception interface for the end component 904, while side portions 918 and 920 define a connection and/or reception interface for the end component 906. Except for the window portion 958, forming part of the window 907, the reception interface of the side portions 914 and 916 for the end component 904 extends from one lateral side of the body 908 to the other lateral side of the body 908. Likewise, except for the window portion 964, forming a part of the window 909, the reception interface of the side portions 918 and 920 for the end component 906 extends from one lateral side of the body 908 to the other lateral side of the body 908.

Side portion 914 includes a flange or projection 922 such that the groove 924 extends from an end 925 of the side portion 914 through the flange 922. Likewise, the side portion 916 includes a flange or projection 930 such that the groove 932 extends from an end 933 of the side portion 916 through the flange 930. Further, likewise, the side portion 918 includes a flange or projection 938 such that the groove 940 extends from an end 941 of the side portion 918 through the flange 938. Even further, likewise, the side portion 920 includes a flange or projection 946 such that the groove 948 extends from an end 949 of the side portion 920 through the flange 946.

Figure 27:
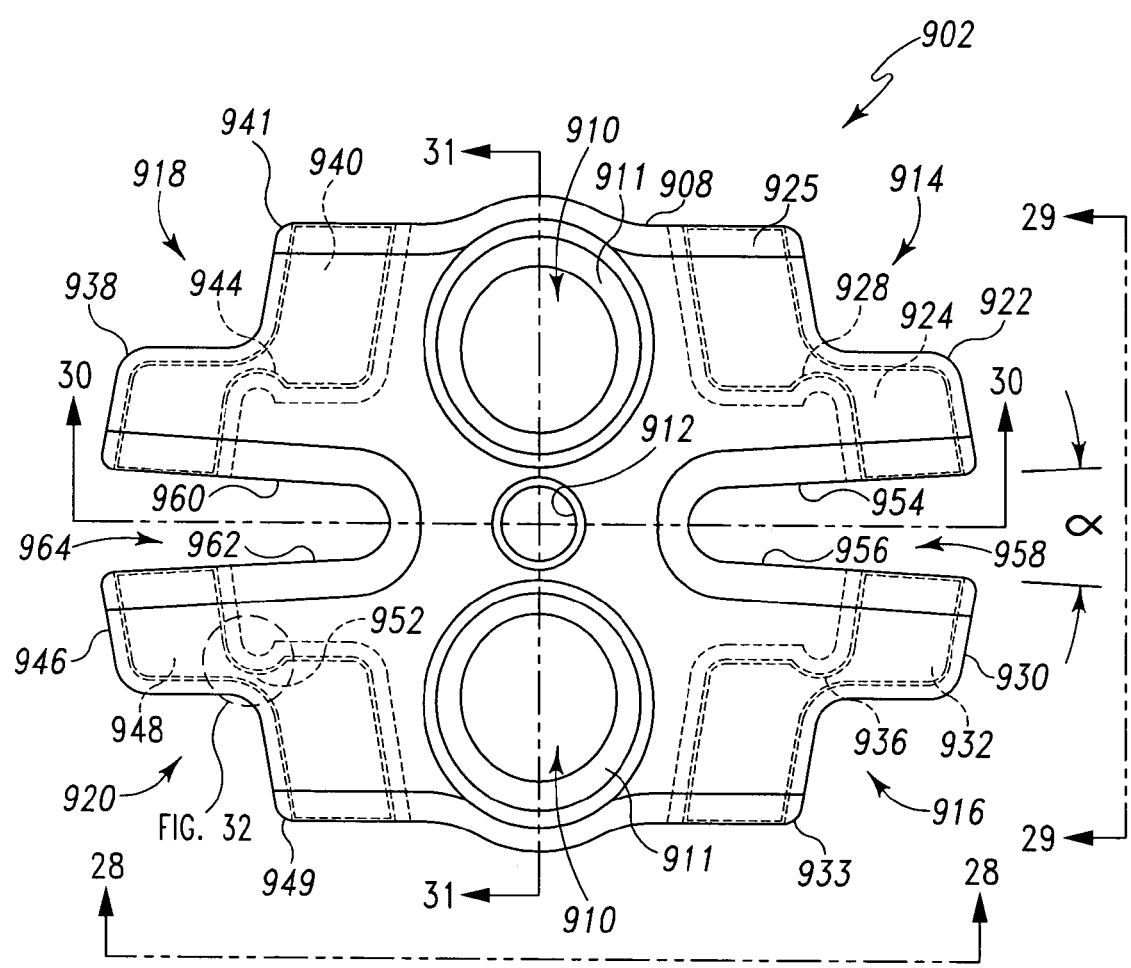
FIG. 27 is a top plan view of the middle plate component of the 2-L dynamic cervical plate of FIG. 26.

Moreover, and still referring specifically to FIG. 27, the window portion 958 is defined by two opposing side surfaces 954 and 956. These side surfaces 954 and 956 are not parallel, but are situated so as to form an angle α relative to an imaginary convergence point of the sides 954 and 956 (i.e. the boss bore 912). Thus the window portion 958 increases in width as it extends longitudinally outward. The window portion 964 is defined by two opposing side surfaces 960 and 962. These side surfaces 960 and 962 are not parallel, but are situated so as to form the angle α relative to an imaginary convergence point of the sides 960 and 962 (i.e. the boss bore 912). Thus the window portion 964 increases in width as it extends longitudinally outward.

Figure 28:
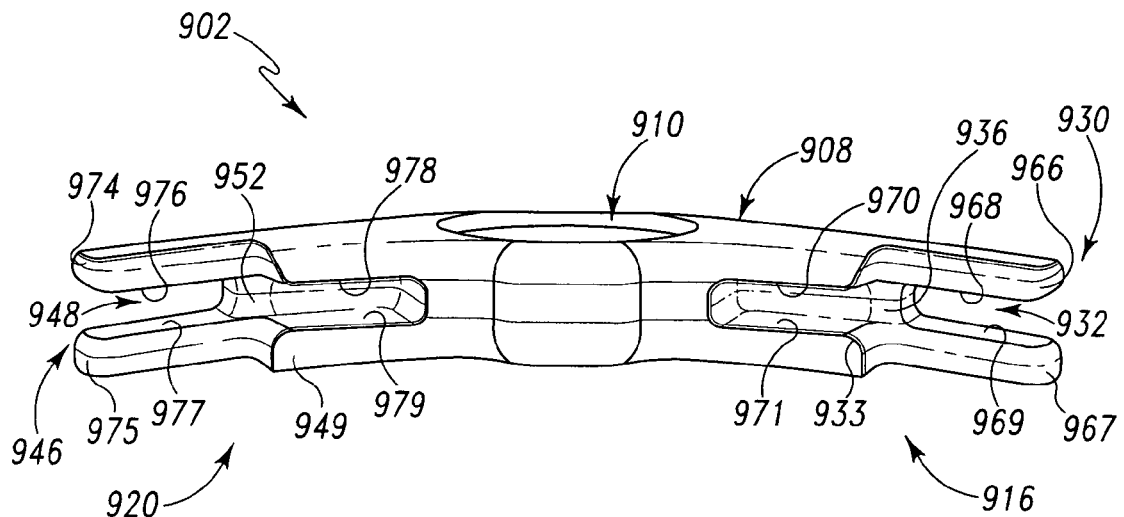
FIG. 28 is a side view of the middle plate component of FIG. 27.

Referring to FIG. 28, one lateral side of the body 908 of the middle component 902 is shown. Particular attention is drawn to the side portions 916 and 920. With respect to the side portion 916, the groove or channel 932 is preferably disposed in the center or middle of the depth (top to bottom per FIG. 28) of the body 908. The flange 930 includes an upper flange portion 966 that defines a lower flange surface 968, and a lower flange portion 967 that defines an upper surface 969. The lower flange surface 968 of the flange portion 966 defines an upper groove surface, while the upper surface 969 of the flange portion 967 defines a lower groove surface. The groove 932 further includes an upper groove surface 970 and a lower groove surface 971 in the end 933 of the body 908. A stop device/detent 936 for limiting the length of unconstrained end component travel is disposed at a junction or transition of the groove 932 from the flange 930 to the end 933 (see e.g. FIG. 27).

Likewise, with respect to the side portion 920, the groove or channel 948 is preferably disposed in the center or middle of the depth (top to bottom per FIG. 28) of the body 908. The flange 946 includes an upper flange portion 974 that defines a lower flange surface 976, and a lower flange portion 975 that defines an upper surface 977. The lower flange surface 976 of the upper flange portion 974 defines an upper groove surface, while the upper surface 977 of the lower flange portion 975 defines a lower groove surface. The groove 948 further includes an upper groove surface 976 and a lower groove surface 977 in the end 949 of the body 908. A stop device/detent 952 for limiting the length of unconstrained end component travel is disposed at a junction or transition of the groove 948 from the flange 946 to the end 949 (see e.g. FIG. 27). The groove 948 is preferably formed essentially identical to the groove 932.

Referring to FIG. 29, an end view of the middle component 902 is shown further illustrating the mating, connecting or receiving nature of the grooves 924 and 932 as well as the like structure of the side portion 914 to the other side portions 916, 918 and 920. Particularly, with respect to the side portion 914, the groove or channel 924 is preferably disposed in the center or middle of the depth (top to bottom per FIG. 29) of the body 908. The flange 922 includes an upper flange portion 982 that defines a lower flange surface 984, and a lower flange portion 983 that defines an upper flange surface 985. The lower flange surface 984 of the upper flange portion 982 defines an upper groove surface, while the upper surface 985 of the lower flange portion 983 defines a lower groove surface. The groove 924 further includes an upper groove surface 986 and a lower groove surface 987 in the end 925 of the body 908. A stop device/detent 928 for limiting the length of unconstrained end component travel is disposed at a junction or transition of the groove 924 from the flange 922 to the end 925 (see e.g. FIG. 27). The groove 924 is preferably formed essentially identical to the groove 932 (but mirrored or flipped).

FIG. 30 shows the flange 938 that is configured like the other flanges 922, 930 and 946. The flange 938 includes an upper flange portion 990 that defines a lower surface 992. The lower surface 992 defines an upper surface for the groove 940. The flange 938 also includes a lower flange portion 991 that defines an upper surface 993. The upper surface 993 defines a lower surface for the groove 940. As illustrated by the diagram below the middle component 902, the body 908 is preferably curved downwardly (at an angle β with respect to a horizontal relative to the plate body 908 from the middle or center of the boss bore 912.

Referring to FIG. 31, the body 908 is shown taken along line 31-31 of FIG. 27. FIG. 31 depicts a second curvature to the body 908 illustrated by the diagram below the middle component 902. Particularly, the body 908 is preferably curved downwardly (at an angle γ with respect to a horizontal relative to the plate body 908 from the middle or center of the boss bore 912. It should be appreciated that either one or both curvatures may be incorporated in the plate 902.

Figure 32:
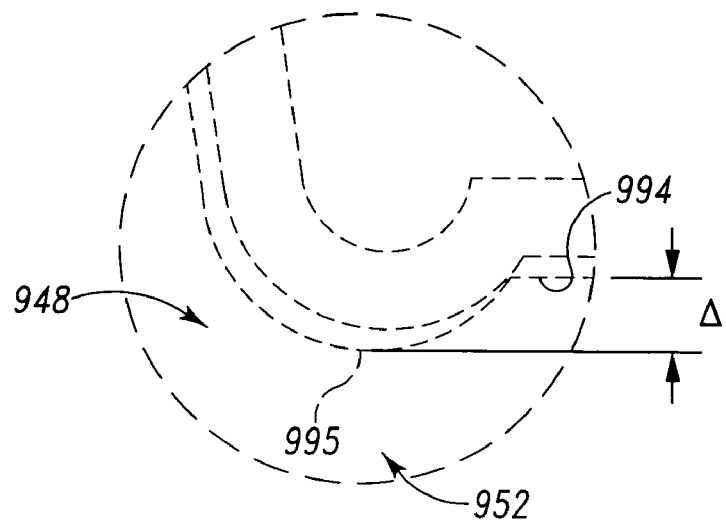
FIG. 32 is an enlarged view of the circled portion of the middle plate component of FIG. 27.

FIG. 32 depicts one of the stops or detent mechanisms, generally designated 952, of the four such detents 928, 936, 944 and 952. The description relative to the detent mechanism 952 is thus applicable to the detent mechanism 928, 936 and 944. The detent mechanism 952 includes a bumped or radiused portion 995 that extends into the groove 948 a distance (measured between a groove wall 994 and the height of the radiused portion 995. When used in conjunction with the detent mechanism of the corresponding tongue of the end component, the detent 995 allows snap or interference fit for sliding interconnectivity but inhibits sliding disassembly.

Figure 33:
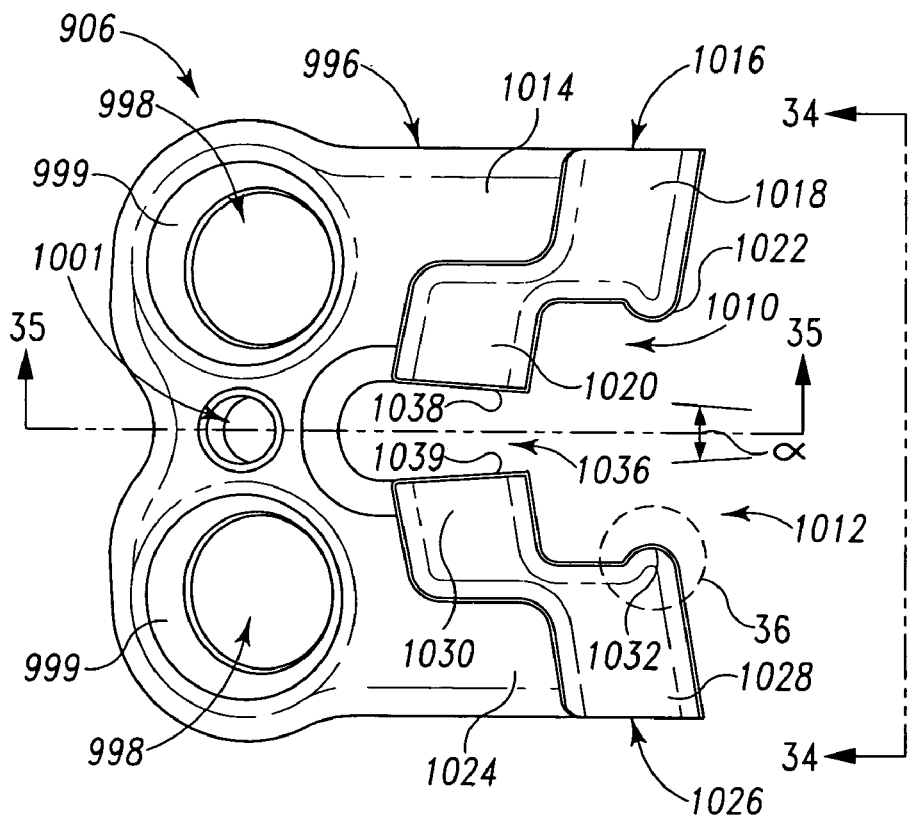
FIG. 33 is a top plan view of the end plate component of the 2-L dynamic cervical plate of FIG. 26.
Figure 34:
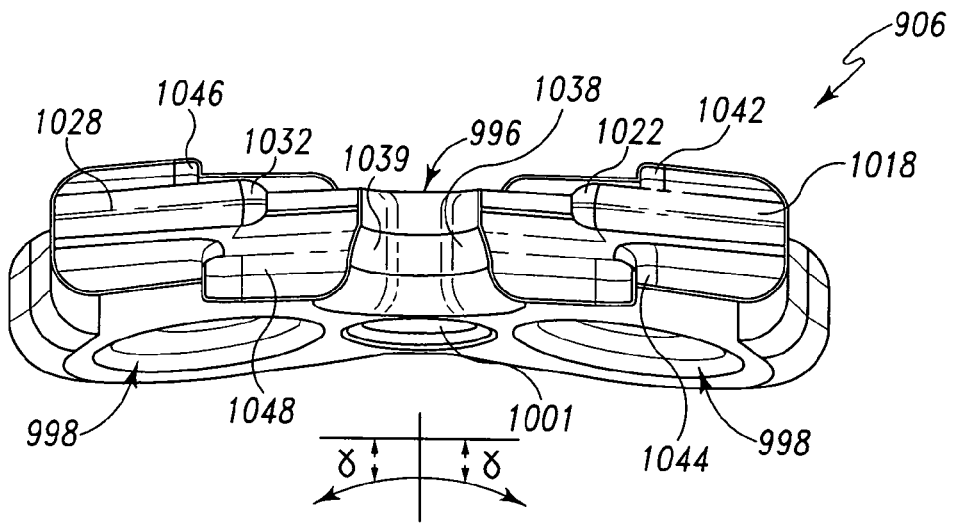
FIG. 34 is an end view of the end plate component of FIG. 33.
Figure 35:
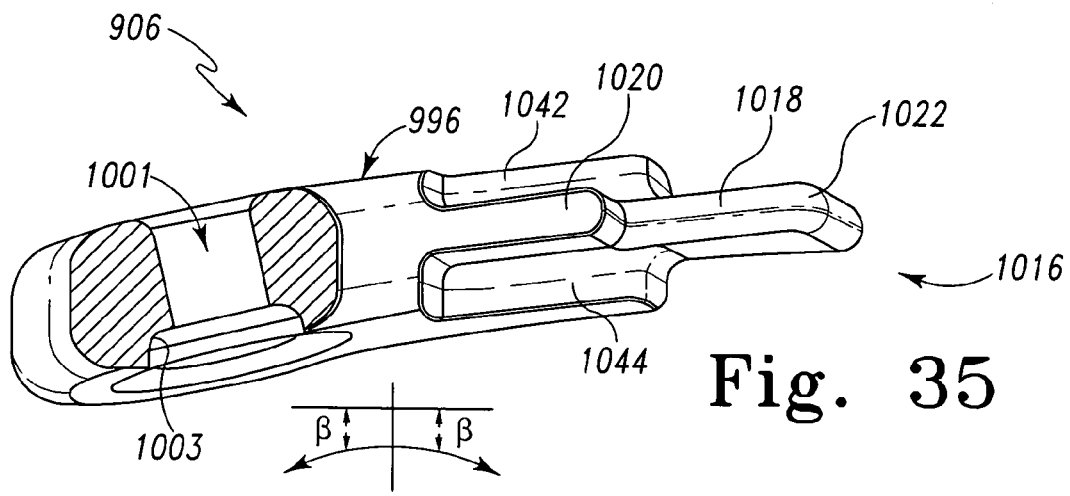
FIG. 35 is a sectional view of the end plate component of FIG. 33 taken along line 35-35 thereof.

With respect to the end component, attention is drawn to FIGS. 33-35 wherein the end component 906, representing both end components 906 and 904, is depicted. It should be appreciated that the end component 906 is used as an end component for both ends of the plate 900. As such, the end component 906 is rotatable 180° (around the plane of the paper) and able to maintain the same configuration. The end plate component 906 has a body 996 having two bone screw bores 998. Each bone screw bore 998 is sized to allow the shank of a bone screw to pass through the bore 998. The bone screw bore, however, includes an annular and truncated conic section ledge 999 that extends radially inwardly to prevent the head of the bone screw to pass through the bore 998. A boss bore 1001 is sized to receive a boss of a clip, cover or the like as described above.

The middle component 906 has a first elongated flange or tongue 1016 extending from a first projection or prong 1014 of the body 996. The middle component 906 further has a second elongated flange or tongue 1026 extending from a second projection or prong 1024 of the body 996. The first tongue 1016 is configured to be slidingly received (assembled) and interconnected with one side portion (either side portion 918 or side portion 916) of the middle component 902, while the second tongue 1026 is configured to be slidingly received (assembled) and interconnected with one side portion (either side portion 920 or side portion 914) of the middle component 902. In this manner, the first and second tongues 1016 and 1026 are slidingly received or interconnected with the grooves of the flanges of a longitudinal end of the middle plate 902. Maximum extension occurs when the ends of the tongues reach the end of the grooves.

The first tongue 1016 is defined by tongue portions 1018 and 1020 whose outer shape is configured to that of the grooves of the flanges of the body 908 of the middle component 902. A stop or detent mechanism 1022 is disposed at a junction or transition between the tongue portions 1018 and 1020. A second tongue 1026 is defined by tongue portions 1028 and 1030 whose outer shape is configured to that of the grooves of the flanges of the body 908 of the middle component 902. A stop or detent mechanism 1032 is disposed at a junction or transition between the tongue portions 1028 and 1030. Moreover, a window portion 1036 as part of a graft window 907 or 909 is defined between the first and second tongues 1016 and 1026.

Particularly a first surface 1038 defines one side of the window portion 1036 while a second surface 1039 defines another, opposing side of the window portion 1036. These side surfaces 1038 and 1039 are not parallel, but are situated so as to form an angle α relative to an imaginary convergence point of the sides 1038 and 1039 (i.e. the boss bore 912 of the middle component 902). Thus, the window portion 1036 increases in width as it extends longitudinally outward from the tongues 1016, 1026 to the bone screw bores 998.

Referring to FIG. 34, an end view of the end component 906 is shown. FIG. 34, in one instance, illustrates a first curvature y extending downwardly on either side of and from a middle line defined through the boss bore 1001 of the body 996 as represented by diagram below the body 996. Moreover, FIG. 34 illustrates that the tongues 1018 and 1028 are situated in the middle of the height of the body 996. As such, the tongue 1018 defines an upper surface end 1042 and a lower surface end 1044. Likewise, the tongue 1028 defines an upper surface end 1046 and a lower surface end 1948. These surfaces abut the ends of the flanges of the middle component 902 when in a fully closed position.

FIG. 35 provides a sectional view of the end component 906 taken along lines 35-35 of FIG. 33. Particularly, as illustrated in FIG. 35 by the diagram below the end component 906, the body 996 is preferably curved downwardly (at an angle β with respect to a horizontal relative to the plate body 996.

Figure 36:
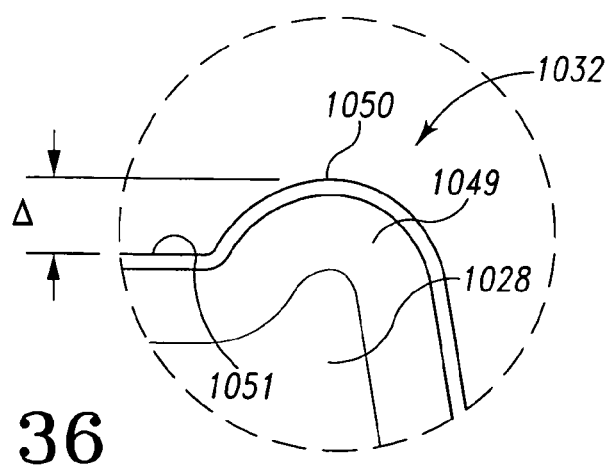
FIG. 36 is an enlarged view of the circled portion of the end plate component of FIG. 33.

FIG. 36 depicts one of the stops or detent mechanisms, generally designated 1032, of the two such detents 1022 and 1032. The description relative to the detent mechanism 1032 is thus applicable to the detent mechanism 1022. The detent mechanism 1032 includes a bumped or radiused portion 1049 a distance (measured between the flange side 1051 and the height 1050 of the radiused portion 1049. When used in conjunction with the detent mechanism of the corresponding grooves of the middle component, the detent 1032 cooperates with the grooves to provide a snap or interference fit for sliding interconnectivity but inhibits sliding disassembly.

It should be appreciate that the principles of the 2-L dynamic plates of FIGS. 14 and 26 (as well as all plates of the present invention) may be utilized as one level dynamic plates, two level dynamic plates, and up to N-level dynamic plates with the minor modification of changing the end configuration of either an end component and/or an end component and middle component. The 2-L dynamic plates of FIGS. 14 and 26, for example, may be modified as a 1-level dynamic plate (two end components) and/or modified as an N-level plate (two end components and N-1 middle components).

With respect to a 1-L plate, this may be accomplished in one manner by modifying one end component to have the same configuration as the configuration of the middle component. With respect to an N-level plate, this may be accomplished by modifying the middle component to have one end configuration the same as an end component, and modifying the middle component accordingly. In summation, the various ends of the end components and the middle components may be mixed to provide mating interconnectivity.

The cervical plates described above are intended for anterior screw fixation to the cervical spine (C2 through T1) for various conditions such as at least the conditions of spondylolisthesis, fracture, spinal stenosis, and tumor.

Each plate is preferably, but not necessarily, formed from titanium (e.g. titanium 6A1-4V ELI per AASTM F-136). Other suitable metals, ceramics may be used if appropriate. Moreover, it should be appreciated that the configuration(s) and/or principles of the 1-L dynamic plate(s) described herein are applicable to and/or may be used in the various 2-L dynamic plates also described herein and n-level dynamic plates. As well, 2-L dynamic plate configurations described herein may be used in the 1-L plates described herein and any n-level dynamic plates. This is particularly true with respect to the various leg or projection configurations and the sliding connectivity thereof.

In general, the preferred embodiment of the present cervical plates will embody curvature in two planes (sagittal and coronal) to more closely resemble the anatomical aspects of the spine. The cervical plates may be provided without curvature or with curvature in one plane as necessary. The plates are made in various sizes (e.g. 14 mm through 110 mm) to accommodate various spines. The plates have a nominal thickness of about 1.8 mm to 3.0 mm and a width of about 18 mm. The plates are configured to accept bone screws having a diameter of about 4.0 through 4.5 mm. Moreover, the bone screw holes of the plates are configured to accommodate both static and variable angle bone screws. This is accomplished by use of a unique pocket design of the bone screw holes. The bone screws are affixed using a typical screw driver (e.g. hexalobullar driver, ×10).

Once the plate has been installed with the appropriate bone screws, the bone screws may be locked via several methods. In one method, a single locking plate locks a pair of screws. The locking plate includes a center post that locks into a cover plate bore in the plate, and which has two configured flanges that are received in the head of the screw. In another form, the cover includes integral locking flanges for the bone screws. The cover and/or locking flanges are preferably made of PEEK, plastic, alloy or titanium.

A plate may be utilized as follows. A plate is placed onto the anterior aspect of a vertebral body of the cervical spine by inserting a 4.0 mm cancellous bone screw or a 4.3 mm expansion screw through the cephalad holes and into the vertebral body. The screw or expansion screws are then inserted into the caudal holes in the plate and inserted into the vertebral bodies of the cervical spine. The locking mechanisms are then inserted in a single step over the entire plate (e.g. a cover), or two locking mechanism are inserted over each set of screws (cephalad and caudel). The locking mechanisms will snap into place.

The present invention also provides for dynamically fusing the cervical spine of a patient via various methods, particularly, but not necessarily, utilizing a cervical plate as described herein. One such method includes the opening of an access aperture in the patient to permit access to an appropriate area of the cervical spine of the patient. A vertebral disc is removed between each vertebra (level) as appropriate (e.g. one disc for a 1-L, two discs for a 2-L, etc.). Bone graft is then sized for placement into the space where the spinal disc has been removed. A dynamic 2-L cervical plate, such as any described herein, is selected for implanting onto the spine (vertebrae). The selected dynamic cervical plate is sized to allow for the best anatomical settling (motion), e.g. between 0 and 4 mm per level, of the vertebral bodies. The selected and sized dynamic plate is placed over the inserted bone graft(s) onto the vertebrae. The graft(s) is then visualized through the window(s) within the dynamic plate for proper fitment. Each section is accomplished in the same manner for proper fitment. The plate is secured onto the spine by bone screws placed through the bone screw bores within the plate components or segments. After each bone screw is attached, a locking mechanism is installed onto/over the bone screws/plate. The aperture is then closed. This method may be utilized with an N-level dynamic plate as described herein.

Another method of dynamically fusing the cervical spine includes providing a dynamic 2-L cervical plate wherein the end components of the provided 2-L dynamic cervical plate move relative to one another utilizing a tongue and groove structure that provides sliding movement relative to one another and that defines a graft window between each level, pair of bone screw bores and/or plate components.

Another method of dynamically fusing the cervical spine includes opening of an access aperture in the patient to permit access to three adjacent vertebra of the cervical spine of the patient to be fused and removing two vertebral discs between the three vertebrae. Bone graft is then sized for placement into the spaces where the vertebral discs have been removed. A two level dynamic cervical plate having a tongue and groove sliding interconnection configuration between end components and a middle component that defines a graft window between each level is provided for implanting onto the three vertebra. The provided dynamic 2-L plate is sized to allow for the best anatomical settling of the vertebral bodies and placed over the inserted bone grafts onto the three vertebra. The grafts are visualized through the graft windows of the dynamic 2-L plate for proper fitment. Thereafter, each component of the two level dynamic plate is attached in sequence for proper fitment. The 2-L plate is assembled prior to placement on the spine. Final fitment on the spine is accomplished by securing each component onto each of the three vertebra by bone screws placed through the bone screw bores of the components. After, a locking mechanism is installed onto each pair of bone screws after each bone screw is attached.

Moreover, any of the methods, such as those above, may include the providing of a 1-level to an N-level (such as a two (2) level) dynamic cervical plate, plate construct, or plate kit, wherein the end segments may be 180° interchangeable relative to a middle segment or an end (with respect to a 1-L plate). The end segments move from 0 to 8 mm or greater depending on size.

The subject invention provides several key attributes that other plates and/or plate systems do not including:

1. The curvatures placed on the window portion of the plate allow the surgeon to align the plate more accurately to the vertebral body.

2. The curvatures placed on the window portion of the plate allow the surgeon to place bone screws more accurately because the bottom of the screw holes mate with a top of the plate window. This provides a positive visual indication that the plate is situated properly.

3. The screw holes have a unique geometry allowing a simple change of screws to utilize the plate as a variable angle screw/plate construct or as a fixed angle screw plate construct.

4. The plate construct may utilize an optional bone screw locking mechanism. The optional screw locking mechanism is a single-piece, snap on cover that is preferably, but not necessarily, made of PEEK or Titanium.

5. In one form, the optional screw locking mechanism attaches into the cervical plate by one of the midline holes. The locking mechanism will cover two screws at one time and lock into the plate using a pronged shaft. Radial projections (propeller like structures) have teeth on the extended ends that mate with the corresponding screws. The teeth lock into the lobes within the screw preventing them from both turning and backing out. This mechanism, like the other, snaps into place but remains removable with the proper instrument.

6. The dynamic plate form of the present invention will allow the fused vertebral bodies to settle onto the graft centered between them. This new dynamic plate and technique will allow fused segments to move, settle or subside which will provide for more constant bone-graft-bone contact. The present dynamic plate design allows the settling to occur in an anatomical fashion, due to plate curvatures. The bodies will translate in stabilized directions on two separate planes (pure translation).

7. The present invention provides the ability to control subsidence of the plate. This is important in order to prevent the plate from migrating into the healthy adjacent disc space. Moreover the present invention aids in preventing the destruction of the host endplate or the graft from unmitigated settling that may lead to pseudarthrosis.

It should be appreciated that the above description is only exemplary of the principles of the subject invention. Therefore, other embodiments are contemplated and within the present scope.

It should be appreciated that the above description is only exemplary of the principles of the subject invention. Therefore, other embodiments are contemplated and within the present scope.

While this invention has been described as having a preferred design, the present invention can be further modified within the spirit and scope of this disclosure. This application is therefore intended to cover any variations, uses, of adaptations of the invention using its general principles. Further, this application is intended to cover such departures from the present disclosure as come within known or customary practice in the art to which this invention pertains and that fall within the limits of the appended claims.

What is claimed is:

1. A two level dynamic cervical plate comprising:
a middle component having a body with a first pair of bone screw bores and first and second longitudinal ends, the first longitudinal end having a first configured groove therein and the second longitudinal end having a second configured groove therein;
a first end component and a second end component, each having a body with a pair of bone screw bores and a connection end, the connection end having a tongue;
a first graft window provided between the first pair of bone screw bores and the pair of bone screw bores of the first end component; and
a second graft window provided between the first pair of bone screw bores and the pair of bone screw bores of the second end component;
wherein the tongue of the first end component is unconstrainedly, slidably interconnected with the groove of the first longitudinal end, and the tongue of the second end component is unconstrainedly, slidably interconnected with the groove of the second longitudinal end.

2. The two level dynamic cervical plate of claim 1, wherein the interconnecting tongue and groove features may be transposed to opposing interconnecting component.

3. The two level dynamic cervical plate of claim 1, wherein the middle component body is curved in two planes of curvature.

4. The two level dynamic cervical plate of claim 1, wherein the first and second end component bodies are curved the two planes of curvature.

5. The two level dynamic plate of claim 1, wherein the tongue and groove sections are the ends and middle segment are angled in one direction and curved in the perpendicular direction.

6. The two level dynamic cervical plate of claim 1, wherein the tongue and groove sections of the ends and middle segment are angled in one direction and curved in the perpendicular directions to provide unconstrained sliding interconnectivity in two planes.

7. The two level dynamic cervical plate of claim 1, wherein the first graft window is formed by a first window portion on the first longitudinal end of the middle component body and a first end window portion of the first end component body, and the second graft window is formed by a second window portion on the second longitudinal end of the middle component body and a second end window portion of the second end component body.

8. The two level dynamic cervical plate of claim 1, wherein the first graft window is defined by opposing sides of the first window portion and the first end window portion that diverge from a center point defined on the middle component, and the second graft window is defined by opposing sides of the second window portion and the second end window portion that diverge from the center point define on the middle component.

9. The two level dynamic cervical plate of claim 1, wherein the middle component includes a boss bore defining a center point.

10. The two level dynamic cervical plate of claim 1, wherein:
the first groove of the first longitudinal end includes a first configured stop;
the second groove of the second longitudinal end of the middle component includes a second stop;
the first tongue of the first end component having a third stop; and
the second tongue of the second end component having a fourth stop;
the first and third stop allowing sliding interconnectivity of the first tongue into the first configured groove, allow unconstrained sliding movement therebetween, but inhibit sliding disassembly between the first tongue and the first configured groove, the second and fourth stop allowing sliding interconnectivity of the second tongue into the second configured groove, allow unconstrained sliding movement therebetween, but inhibit sliding disassembly between the second tongue and the second configured groove.

11. The two level dynamic cervical plate of claim 1, wherein the interconnecting tongue and groove features may be transposed to an opposing interconnecting component.

12. A dynamic two level cervical plate comprising:
a middle plate component having a first pair of bone screw bores situated thereon, a first pair of middle component projections extending from a first side thereof and a second pair of middle component projections extending from a second side thereof, the first and second pairs of middle component projections each having a configured receiving groove therein;
a first end plate component and a second end plate component, each having a pair of bone screw bores, and a pair of end plate component projections extending from a side thereof, the pair of end plate component projections having one of an end plate component groove and an end plate component channel complementary to that of the first and second pairs of middle plate component projections, the projections of the first and second end plate components in unconstrained sliding interconnectivity with the middle plate component projections to allow varying distances between the pairs of bone screw bores after attachment;
a first graft window defined by the first pair of middle component projections and the first pair of end plate components of the first end plate, wherein the first graft window is configured to provide access to a first graft between a first vertebrae and a second vertebrae; and
a second graft window defined by the second pair of middle component projections and the second pair of end plate components of the second end plate, wherein the second graft window is configured to provide access to a second graft between the second vertebrae and a third vertebrae.

13. The two level dynamic cervical plate of claim 12, wherein the interconnecting tongue and groove features may be transposed to opposing interconnecting components.

14. The dynamic two level cervical plate of claim 12, wherein the middle component body is curved in two planes of curvature.

15. The dynamic two level cervical plate of claim 12, wherein the first and second end plate components are curved the two planes of curvature.

16. The dynamic two level cervical plate of claim 12, wherein the first graft window is formed by a first window portion defined by the first pair of middle component projections and a first end window portion of the first end plate component projections, and the second graft window is formed by a second window portion defined by the second pair of middle component projections and a second end window portion of the second end plate component projections.

17. The dynamic two level cervical plate of claim 12, wherein the first graft window is defined by opposing sides of the first window portion and the first end window portion that diverge from a center point defined on the middle component, and the second graft window is defined by opposing sides of the second window portion and the second end window portion that diverge from the center point define on the middle component.

18. The dynamic two level cervical plate of claim 12, wherein the middle component includes a boss bore defining a center point.

19. The dynamic two level cervical plate of claim 12, wherein:
    the first receiving groove includes a first stop;
    the second receiving groove includes a second stop;
    the first projections have a third stop; and
    the second projections have a fourth stop;
    the first and third stops allowing sliding interconnectivity of the first projections into the first receiving groove, allow unconstrained sliding movement therebetween, hut inhibit sliding disassembly between the first projections and the first receiving groove, the second and fourth stops allowing sliding interconnectivity of the second projections into the second receiving grooves, allow unconstrained sliding movement therebetween, but inhibit sliding disassembly between the second projections and the second receiving groove.

20. The dynamic two level cervical plate of claim 12, wherein the access provided by the first graft window or the second graft window is visual access.

21. The dynamic two level cervical plate of claim 20, wherein the first graft window extends from adjacent the bone screw bores on the first end plate component to adjacent the first pair of bone screw bores on the middle plate component.

22. The dynamic two level cervical plate of claim 21, wherein the second graft window extends from adjacent the bone screw bores on the second end plate component to adjacent the first pair of bone screw bores on the middle plate component.

* * * * *